(12) United States Patent
Kietzmann

(10) Patent No.: US 12,397,102 B2
(45) Date of Patent: *Aug. 26, 2025

(54) PACKAGING ASSEMBLY

(71) Applicant: Sanofi, Paris (FR)

(72) Inventor: Hardy Kietzmann, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/605,157

(22) Filed: Mar. 14, 2024

(65) Prior Publication Data

US 2024/0358912 A1    Oct. 31, 2024

Related U.S. Application Data

(63) Continuation of application No. 17/825,790, filed on May 26, 2022, now Pat. No. 11,944,777, which is a
(Continued)

(30) Foreign Application Priority Data

Feb. 24, 2017    (EP) ..................... 17305211

(51) Int. Cl.
*A61M 5/00*    (2006.01)
*G07C 9/00*    (2020.01)
(Continued)

(52) U.S. Cl.
CPC ......... *A61M 5/002* (2013.01); *G07C 9/00174* (2013.01); *G08B 5/36* (2013.01);
(Continued)

(58) Field of Classification Search
CPC . G08B 21/185; A61M 15/00; A61M 15/0001; A61M 15/08; A61M 5/20;
(Continued)

(56) References Cited

U.S. PATENT DOCUMENTS 2,698,155 A    12/1954    Bowman
4,349,338 A    9/1982    Heppler
(Continued)

FOREIGN PATENT DOCUMENTS

CN    2568179    8/2003
CN    1630604    6/2005
(Continued)

OTHER PUBLICATIONS

PCT International Preliminary Report on Patentability in International Appln. No. PCT/EP2016/079038, dated Jun. 5, 2018, 7 pages.
(Continued)

*Primary Examiner* — Brian A Zimmerman
*Assistant Examiner* — Anthony D Afrifa-Kyei
(74) *Attorney, Agent, or Firm* — Fish & Richardson P.C.

(57) ABSTRACT

A packaging assembly comprises a case configured to at least partially contain a plurality of injection devices for delivering a medicament; a light sensor configured to detect light incident on the packaging assembly; and a wireless communication module configured to establish a wireless connection with at least one external device conditional on an intensity of light detected by the light sensor exceeding a threshold light intensity.

20 Claims, 8 Drawing Sheets

Related U.S. Application Data continuation of application No. 16/487,006, filed as application No. PCT/EP2018/054464 on Feb. 23, 2018, now Pat. No. 11,369,732.

(51) Int. Cl.

| | | |
|---|---|---|
| *G08B 5/36* | (2006.01) | |
| *G16H 20/17* | (2018.01) | |
| *H04W 76/40* | (2018.01) | |
| *A61M 5/20* | (2006.01) | |

(52) U.S. Cl.
CPC ............ *G16H 20/17* (2018.01); *H04W 76/40* (2018.02); *A61M 5/20* (2013.01); *A61M 2205/18* (2013.01); *A61M 2205/3306* (2013.01); *A61M 2205/3368* (2013.01); *A61M 2205/3584* (2013.01); *A61M 2205/502* (2013.01); *A61M 2205/52* (2013.01); *A61M 2205/581* (2013.01); *A61M 2205/583* (2013.01); *A61M 2205/587* (2013.01); *A61M 2205/6054* (2013.01); *A61M 2205/6072* (2013.01); *A61M 2205/8206* (2013.01)

(58) Field of Classification Search
CPC .... A61M 5/2053; A61M 5/31; A61M 5/3157; A61M 11/007; A61M 2005/206; A61M 2005/2073; A61M 2205/14; A61M 2205/18; A61M 2205/3306; A61M 2205/3375; A61M 2205/3553; A61M 2205/3561; A61M 2205/3569; A61M 2205/3584; A61M 2205/3592; A61M 2205/43; A61M 2205/50; A61M 2205/52; A61M 2205/581; A61M 2205/582; A61M 2205/583; A61M 2205/587; A61M 2205/8206; A61M 2205/8212; A61M 2230/04; A61M 2230/20; A61M 2230/201; A61M 2230/42; A61M 5/3202; A61M 5/5086; G06F 19/00; G06F 19/3468; G06F 19/3462; G09B 9/00; G16H 20/17; H04B 1/3827; H04W 4/008; H04W 4/80; Y02A 90/26; A61J 1/035; A61J 7/0418; A61J 7/0481; A61J 2200/30; A61J 2205/70; A61J 7/0436

See application file for complete search history.

(56) References Cited

U.S. PATENT DOCUMENTS

| | | | |
|---|---|---|---|
| 4,572,403 A | 2/1986 | Benaroya | |
| 4,903,832 A | 2/1990 | Stewart | |
| 4,915,233 A | 4/1990 | Smith | |
| 5,522,503 A | 6/1996 | Halbich | |
| 5,915,558 A | 6/1999 | Girvetz | |
| 5,970,974 A | 10/1999 | Van der Linden et al. | |
| 6,056,118 A | 5/2000 | Hargus et al. | |
| 6,464,506 B1 | 10/2002 | Dickerson | |
| 6,595,362 B2 | 7/2003 | Penney et al. | |
| 6,955,259 B1 | 10/2005 | Jesse | |
| 7,434,686 B2 | 10/2008 | Prindle | |
| 7,522,477 B1 | 4/2009 | Sheldon | |
| 8,544,645 B2 | 10/2013 | Edwards et al. | |
| 8,584,486 B1 | 11/2013 | Allard et al. | |
| 9,311,452 B2 | 4/2016 | Dickie et al. | |
| 10,398,524 B2 | 9/2019 | Denny et al. | |
| 10,588,823 B1 | 3/2020 | Arora | |
| 10,869,962 B2 | 12/2020 | Kietzmann et al. | |
| 11,103,632 B2 | 8/2021 | Kietzmann et al. | |
| 11,103,633 B2 | 8/2021 | Kietzmann et al. | |
| 11,278,660 B2 | 3/2022 | Kietzmann et al. | |
| 11,369,732 B2 * | 6/2022 | Keitzmann | A61M 5/002 |
| 11,565,034 B2 | 1/2023 | Keitzmann | |
| 11,724,021 B2 | 8/2023 | Kietzmann | |
| 11,944,777 B2 | 4/2024 | Keitzmann | |
| 11,951,274 B2 | 4/2024 | Kietzmann et al. | |
| 12,115,336 B2 | 10/2024 | Kietzmann et al. | |
| 12,133,964 B2 | 11/2024 | Kietzmann et al. | |
| 2002/0050462 A1 | 5/2002 | Penney et al. | |
| 2002/0158058 A1 | 10/2002 | Faries et al. | |
| 2004/0069667 A1 | 4/2004 | Tomellini et al. | |
| 2005/0256388 A1 | 11/2005 | Susi | |
| 2007/0214812 A1 | 9/2007 | Wagner et al. | |
| 2007/0215782 A1 | 9/2007 | Phung et al. | |
| 2007/0246396 A1 | 10/2007 | Brollier | |
| 2008/0306443 A1 | 12/2008 | Neer et al. | |
| 2009/0115598 A1 | 5/2009 | Carlson | |
| 2009/0134181 A1 | 5/2009 | Wachman et al. | |
| 2011/0218502 A1 | 9/2011 | Iio et al. | |
| 2012/0232520 A1 | 9/2012 | Sloan et al. | |
| 2013/0002795 A1 | 1/2013 | Shavelsky et al. | |
| 2013/0211323 A1 | 8/2013 | Lee | |
| 2013/0289536 A1 | 10/2013 | Croizat et al. | |
| 2014/0018733 A1 | 1/2014 | Sjolund et al. | |
| 2014/0018744 A1 | 1/2014 | Holmqvist | |
| 2014/0155827 A1 | 6/2014 | Ostrander et al. | |
| 2014/0165614 A1 | 6/2014 | Manning et al. | |
| 2014/0252927 A1 | 9/2014 | Denny et al. | |
| 2014/0350720 A1 | 11/2014 | Lehmann et al. | |
| 2015/0014210 A1 | 1/2015 | Priebe et al. | |
| 2015/0048100 A1 | 2/2015 | Dickie et al. | |
| 2015/0196711 A1 | 7/2015 | Edwards et al. | |
| 2015/0251839 A1 | 9/2015 | Denny et al. | |
| 2015/0283341 A1 | 10/2015 | Adams et al. | |
| 2015/0317455 A1 | 11/2015 | Lehmann et al. | |
| 2015/0378314 A1 | 12/2015 | Nakabayashi | |
| 2016/0129182 A1 | 5/2016 | Schuster et al. | |
| 2016/0162832 A1 | 6/2016 | Thompson et al. | |
| 2016/0199592 A1 | 7/2016 | Eggert et al. | |
| 2016/0232877 A1 | 8/2016 | Cho et al. | |
| 2016/0243318 A1 | 8/2016 | Despa et al. | |
| 2017/0056605 A1 | 3/2017 | Kondo et al. | |
| 2017/0087059 A1 | 3/2017 | Rodriguez et al. | |
| 2017/0224588 A1 | 8/2017 | Kitson et al. | |
| 2017/0368260 A1 | 12/2017 | McCullough et al. | |
| 2018/0001015 A1 | 1/2018 | Ziegner | |
| 2018/0015218 A1 | 1/2018 | Welsch | |
| 2018/0236181 A1 | 8/2018 | Marlin et al. | |
| 2018/0256811 A1 | 9/2018 | Kietzmann et al. | |
| 2018/0256812 A1 | 9/2018 | Kietzmann et al. | |
| 2019/0030329 A1 | 1/2019 | Hannaman et al. | |
| 2020/0054820 A1 | 2/2020 | Kietzmann et al. | |
| 2020/0397977 A1 | 12/2020 | Kietzmann | |
| 2020/0397978 A1 | 12/2020 | Kietzmann | |
| 2021/0015994 A1 | 1/2021 | Kietzmann et al. | |
| 2021/0046239 A1 | 2/2021 | Kietzmann | |
| 2021/0060235 A1 | 3/2021 | Kietzmann et al. | |
| 2021/0353852 A1 | 11/2021 | Kietzmann et al. | |
| 2022/0296805 A1 | 9/2022 | Keitzmann | |
| 2023/0398283 A1 | 12/2023 | Keitzmann | |
| 2023/0414860 A1 | 12/2023 | Kietzmann et al. | |

FOREIGN PATENT DOCUMENTS

| | | |
|---|---|---|
| CN | 2744339 | 12/2005 |
| CN | 1871046 | 11/2006 |
| CN | 101073533 | 11/2007 |
| CN | 101116077 | 1/2008 |
| CN | 101152620 | 4/2008 |
| CN | 101318037 | 12/2008 |
| CN | 101384237 | 3/2009 |
| CN | 101405749 | 4/2009 |
| CN | 201352126 | 11/2009 |
| CN | 101912641 | 12/2010 |
| CN | 201664175 | 12/2010 |
| CN | 201829032 | 5/2011 |
| CN | 201877103 | 6/2011 |
| CN | 102202703 | 9/2011 |
| CN | 201979271 | 9/2011 |
| CN | 102542176 | 7/2012 |
| CN | 202287671 | 7/2012 |

(56) References Cited

FOREIGN PATENT DOCUMENTS

| | | |
|---|---|---|
| CN | 202311770 | 7/2012 |
| CN | 202426229 | 9/2012 |
| CN | 102770170 | 11/2012 |
| CN | 102946459 | 2/2013 |
| CN | 103380059 | 10/2013 |
| CN | 103619378 | 3/2014 |
| CN | 203634510 | 6/2014 |
| CN | 104055678 | 9/2014 |
| CN | 203970030 | 12/2014 |
| CN | 204050542 | 12/2014 |
| CN | 104363940 | 2/2015 |
| CN | 104491951 | 4/2015 |
| CN | 204351461 | 5/2015 |
| CN | 204467263 | 7/2015 |
| CN | 104870032 | 8/2015 |
| CN | 104955435 | 9/2015 |
| CN | 104956416 | 9/2015 |
| CN | 204766326 | 11/2015 |
| CN | 204890775 | 12/2015 |
| CN | 105307717 | 2/2016 |
| CN | 205041890 | 2/2016 |
| CN | 205098506 | 3/2016 |
| CN | 205872707 | 1/2017 |
| DE | 20201026 | 4/2002 |
| DE | 10132869 | 10/2002 |
| EP | 2119423 | 11/2009 |
| EP | 2357013 | 8/2011 |
| EP | 3010660 | 4/2016 |
| EP | 3103493 | 12/2016 |
| EP | 3449575 | 3/2019 |
| GB | 2520054 | 5/2015 |
| GB | 2520181 | 5/2015 |
| GB | 2552539 A | 1/2018 |
| JP | S51-93401 | 7/1976 |
| JP | S61-055792 U | 4/1986 |
| JP | H06-511183 | 12/1994 |
| JP | H10-033639 | 2/1998 |
| JP | 2001-503302 | 3/2001 |
| JP | 2002-504397 | 2/2002 |
| JP | 2007-510469 | 4/2007 |
| JP | 2008-114008 | 5/2008 |
| JP | 2012-217802 | 11/2012 |
| JP | 3189723 U | 3/2014 |
| JP | 2014-079483 | 5/2014 |
| JP | 2014-111173 | 6/2014 |
| JP | 2014-126231 | 7/2014 |
| JP | 2015-531653 | 11/2015 |
| JP | 2016-518879 | 6/2016 |
| JP | 2016-529016 | 9/2016 |
| KR | 10-1564249 | 11/2015 |
| RU | 2405532 | 12/2010 |
| WO | WO 1994/004966 | 3/1994 |
| WO | WO 1998/019647 | 5/1998 |
| WO | WO 1999/043283 | 9/1999 |
| WO | WO 2001/087739 | 11/2001 |
| WO | WO 2003/062091 | 7/2003 |
| WO | WO 2005/046559 | 5/2005 |
| WO | WO 2006/086735 | 8/2006 |
| WO | WO 2007/082543 | 7/2007 |
| WO | WO 2007/107562 | 9/2007 |
| WO | WO 2007/126851 | 11/2007 |
| WO | WO 2007/135578 | 11/2007 |
| WO | WO 2010/055608 | 5/2010 |
| WO | WO 2011/054000 | 5/2011 |
| WO | WO 2011/070329 | 6/2011 |
| WO | WO 2011/080092 | 7/2011 |
| WO | WO 2012/112631 | 8/2012 |
| WO | WO 2012/145752 | 10/2012 |
| WO | WO 2013/025520 | 2/2013 |
| WO | WO 2013/050342 | 4/2013 |
| WO | WO 2013/120776 | 8/2013 |
| WO | WO 2014/043054 | 3/2014 |
| WO | WO 2014/096146 | 6/2014 |
| WO | WO 2014/143815 | 9/2014 |
| WO | WO 2014/159933 | 10/2014 |
| WO | WO 2014/184293 | 11/2014 |
| WO | WO 2014/192888 | 12/2014 |
| WO | WO 2014/204958 | 12/2014 |
| WO | WO 2015/032715 | 3/2015 |
| WO | WO 2015/085019 | 6/2015 |
| WO | WO 2015/151900 | 10/2015 |
| WO | WO 2016/014365 | 1/2016 |
| WO | WO 2016/022760 | 2/2016 |
| WO | WO 2016/033507 | 3/2016 |
| WO | WO 2016/142726 | 9/2016 |
| WO | WO 2017/186402 | 11/2017 |
| WO | WO 2018/153945 | 8/2018 |
| WO | WO 2018/154033 | 8/2018 |
| WO | WO 2018/172858 | 9/2018 |

OTHER PUBLICATIONS

PCT International Preliminary Report on Patentability in International Appln. No. PCT/EP2016/079039, dated Jun. 5, 2018, 7 pages.
PCT International Preliminary Report on Patentability in International Appln. No. PCT/EP2016/079040, dated Jun. 5, 2018, 6 pages.
PCT International Preliminary Report on Patentability in International Appln. No. PCT/EP2018/054323, dated Aug. 27, 2019, 7 pages.
PCT International Preliminary Report on Patentability in International Appln. No. PCT/EP2018/054464, dated Aug. 27, 2019, 7 pages.
PCT International Search Report and Written Opinion in International Appln. No. PCT/EP2016/079038, dated Feb. 17, 2017, 10 pages.
PCT International Search Report and Written Opinion in International Appln. No. PCT/EP2016/079039, dated Feb. 21, 2017, 9 pages.
PCT International Search Report and Written Opinion in International Appln. No. PCT/EP2016/079040, dated Feb. 6, 2017, 8 pages.
PCT International Search Report and Written Opinion in International Appln. No. PCT/EP2018/054323, dated May 4, 2018, 11 pages.
PCT International Search Report and Written Opinion in International Appln. No. PCT/EP2018/054464, dated May 23, 2018, 10 pages.
U.S. Appl. No. 15/779,657, filed May 29, 2018, Hardy Kietzmann.
U.S. Appl. No. 17/386,746, filed Jul. 28, 2021, Hardy Kietzmann.
U.S. Appl. No. 18/466,564, filed Sep. 13, 2023, Hardy Kietzmann.
U.S. Appl. No. 15/779,650, filed May 29, 2018, Hardy Kietzmann.
U.S. Appl. No. 17/082,093, filed Oct. 28, 2020, Hardy Kietzmann.
U.S. Appl. No. 15/779,747, filed May 29, 2018, Hardy Kietzmann.
U.S. Appl. No. 17/063,962, filed Oct. 6, 2020, Hardy Kietzmann.
U.S. Appl. No. 16/487,006, filed Aug. 19, 2019, Hardy Keitzmann.
U.S. Appl. No. 17/825,790, filed May 26, 2022, Hardy Keitzmann.
U.S. Appl. No. 16/487,013, filed Aug. 19, 2019, Hardy Keitzmann.
U.S. Appl. No. 17/088,269, filed Nov. 3, 2020, Hardy Kietzmann.
U.S. Appl. No. 18/333,999, filed Jun. 13, 2023, Hardy Kietzmann.

* cited by examiner

PACKAGING ASSEMBLY

CROSS-REFERENCE TO RELATED APPLICATIONS

The present application is a continuation of U.S. patent application Ser. No. 17/825,790, filed May 26, 2022, which is a continuation of U.S. patent application Ser. No. 16/487,006, filed on Aug. 19, 2019, now U.S. Pat. No. 11,369,732, which is a national stage entry of International Patent Application No. PCT/EP2018/054464, filed on Feb. 23, 2018, and claims priority to European Application No. EP 17305211.9, filed on Feb. 24, 2017, the disclosures of which are incorporated herein by reference.

TECHNICAL FIELD

The application relates to a packaging assembly for a medicament and, in particular, although not exclusively, to a packaging assembly configured to communicate with an external device.

BACKGROUND

Patients suffering chronic disease require regular treatment with medicaments, e.g. on the basis of a predefined schedule. Particular medicaments require refrigerated storage, and are often stored refrigerated in a household refrigerator or fridge. In a home treatment environment, the patient stores the medicament in their fridge and administers a predefined dose as required. Hence, the medicament is typically provided in a secondary packaging for convenient placement and storage in the household fridge. However, the medicament must be stored together with other items that require constant refrigeration, such as foodstuffs and beverages.

Depending on the dosage form of the medicament, the secondary packaging containing the medicament may store a primary packed medicament itself, or may store one or more different kinds of drug delivery devices. For instance, the medicament may be provided in a pre-filled syringe or pen-type injector.

A medicament may have a predefined dosing schedule which requires the administration of a dose at relatively long intervals, for instance every two or four weeks, or once a month. The medicament may be provided in a secondary packaging containing several doses which may be stored in the fridge for 1 to 6 months for instance. It can be difficult for patients to keep track of each scheduled dosing time.

SUMMARY

According to an embodiment, a packaging assembly is provided according to the claims.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying drawings, in which.

DETAILED DESCRIPTION

Figure 1:
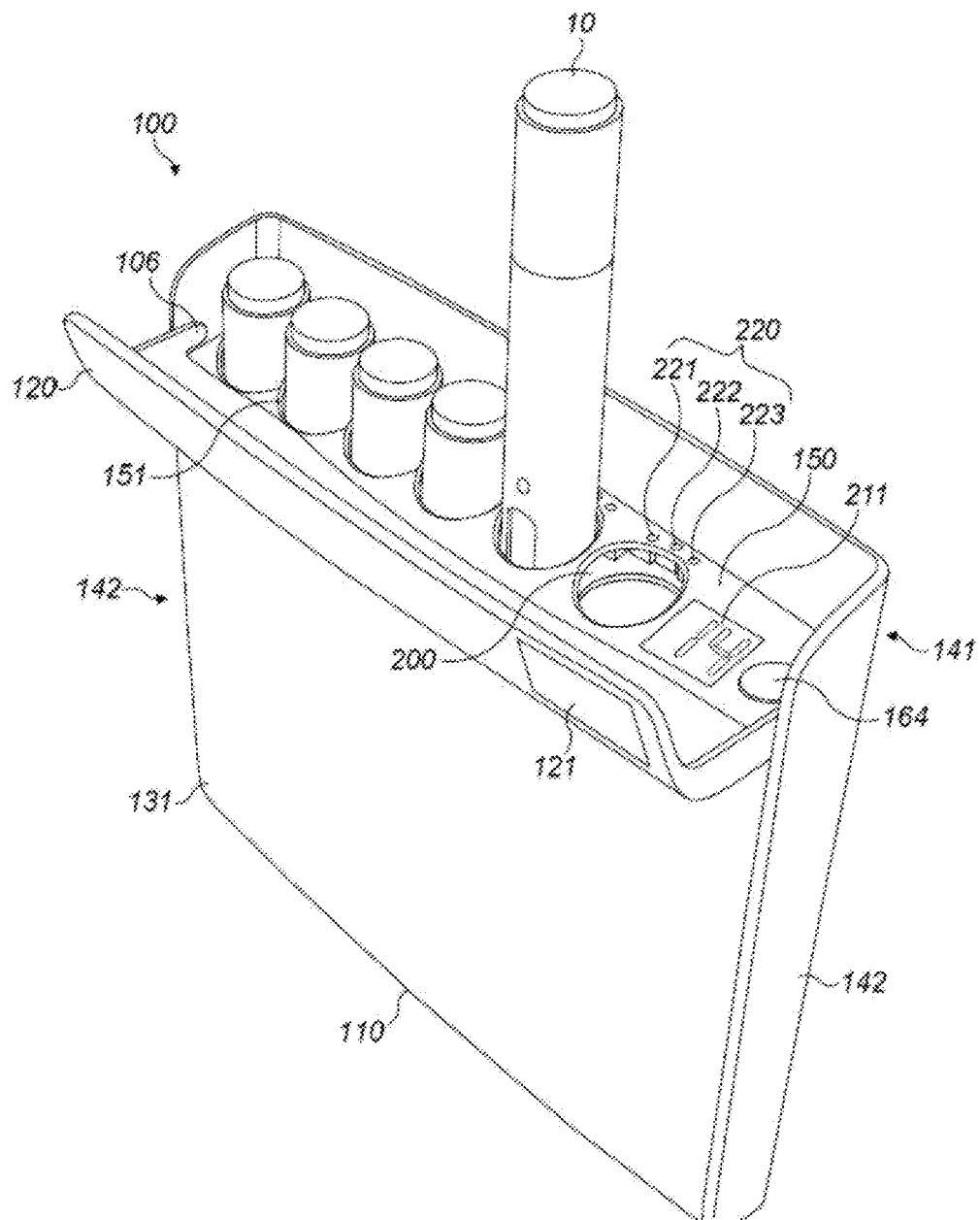
FIG. 1 is an isometric view of a packaging assembly according to a first exemplary embodiment.

Embodiments of the disclosure provide a packaging assembly configured to contain and store a plurality of injection devices for delivering a medicament. An injection device is an example of a drug delivery device and may be a pen-injector or an auto-injector. The packaging assembly is configured to establish communication with an external device. The packaging assembly may be configured to provide an audio and/or visual reminder to a patient at a scheduled dosing time for the medicament. The packaging assembly may further include one or more user interface elements for providing the patient with a status and information relating to a status of the packaging assembly. The packaging assembly provides a predictable, easy to use operation for the patient.

The packaging assembly may be stored in a household refrigerator or fridge. The packaging assembly may include a door open sensor to determine whether or not the fridge is open. The packaging assembly may be configured to establish communication with an external device conditional on the fridge door being open. The packaging assembly provides information easily and intuitively via the external device, and allows safe storage in a fridge for convenient and discreet use by the patient.

A drug delivery device, as described herein, may be configured to inject a medicament into a patient. For example, delivery could be sub-cutaneous, intra-muscular, or intravenous. Such an injection device could be operated by a patient or care-giver, such as a nurse or physician, and can include various types of safety syringe, pen-injector, or auto-injector. The injection device can include a cartridge-based system that requires piercing a sealed ampule before use. Volumes of medicament delivered with these various injection devices can range from about 0.2 ml to about 3 ml. Yet another injection device can be represented by a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described injection devices may also be customized to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, an injection device will often include a hollow needle ranging from about 25 to about 31 Gauge in size. Common sizes are 27 and 29 Gauge.

The injection devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanisms to cause the automated function. For example, a user may depress a needle sleeve against their body to cause injection of a medicament. In other devices, a user may be required to depress a button and retract a needle shield to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

With reference to FIG. 1, a packaging assembly 100 according to exemplary embodiments is shown. The packaging assembly 100 comprises a case 110 having a lid 120. The case 110 comprises a lower face 130, an upper face 141, and two side walls 142. The lower face 131 is curved so as to meet the upper face 141 at the rear of the device. At a front end of the case 110, an opening is formed between lower face 131, the upper face 141 and the two side walls 142.

The lid 120 of the case 110 is arranged to cover the opening of the case 110. The lid 120 is attached between the two side walls 142 of the case 110 in a hinged manner. The lid 120 can be freely moved in a hinged manner between a closed position and an open position. In the closed position, the lid 120 is arranged to cover the opening of the case 110. In the open position, the opening of the case 110 is uncovered and an interior of the case 110 can be accessed.

The lid 120 may comprise a latching mechanism to hold the lid 120 in the closed position. The latching mechanism may comprise a protruding part arranged at an edge of the lid 120. The protruding part may be configured to engage with a corresponding feature in the case 110 when the lid is in the closed position. The protruding part may be flexible or retractable to disengage from the case 110 and allow the lid 120 to move to the open position. The lid 120 may further comprise a locking mechanism 270 configured to prevent the lid 120 from moving to the open position. The locking mechanism may be controlled electronically.

The case 110 is configured to hold and store a plurality of injection devices 10. A length of the case 110, measured between the rear of the case and the lid 120, is sufficient to accommodate the length of each of the injection devices 10. The length of the case may be between 160 mm and 180 mm. A depth of the case 110, measured between the upper face 141 and the lower face 131, is sufficient to accommodate the width of each of the injection devices 10. The depth of the case may be between 30 mm and 40 mm. A width of the case 110, measured between the two side walls 142, is sufficient to accommodate six injection devices 10. The width of the case may be between 180 mm and 200 mm. In some examples, the case may be 188.7 mm wide, 174.7 mm high and 34 mm deep.

As shown in FIG. 1, the lower face 131 of the case 110 is shorter than the upper face 141. The lid 120 extends from a front edge of the lower face 131 to a front edge of the upper face 141. The lid 120 is curved. The curve allows the lid 120 to form the front and a portion of the bottom of the case 110 in the closed position. Other lid configurations are also contemplated.

The lower face 131, the upper face 141 and the two side walls 142 are formed from an opaque material, for example, an opaque plastic material. The lid 120 is formed from a translucent or frosted material, for example, a clear plastic material with a frosted coating or a treated surface. A portion of the lid 120 is clear and transparent to form a viewing window 121 through the lid 120.

The case 110 further comprises a panel 150 arranged within the opening. The panel 150 is visible only when the lid 120 of the case 110 is in an open position; when the lid 120 is in the closed position, the lid obscures the panel 150 from view. The panel 150 comprises a plurality of openings 151. The openings 151 are configured to hold a corresponding plurality of injection devices 10. The openings 151 in the panel 150 are circular in shape. The openings 151 may be square shaped, or rectangular shaped to accommodate other sizes of injection device 10. The width of each opening is sufficient to accommodate the width of each injection device 10. The panel 150 comprises a row of six openings, so as to hold six injection devices 10 arranged in a row along a width of the case 110.

The packaging assembly 100 may be configured to hold more than six, or fewer than six injection devices 10 in the case 110.

The lid 120 may be configured to retain the plurality of injection devices 10 in position within the case 110 when in the closed position. The lid 120 may be arranged in the closed position to prevent the injection devices 10 from falling or sliding out of the case 110. Each injection device 10 may be retained in position within the corresponding opening 151 by a friction fit with the opening 151.

A retention mechanism may retain the plurality of injection devices 10 in position within the openings 151. The retention mechanism may comprise a mechanical catch configured to engage with each injection device 10, for example, a sprung push-catch push-release mechanism. The injection device 10 is pushed into the opening 151 and pushed against a spring of the retention mechanism to engage a catch. The injection device 10 is pushed a second time to release the catch. A release button or switch may be provided for each of the openings 151, which is configured to release the catch of the retention mechanism when pressed.

A user may receive the packaging assembly 100 in an empty condition. When the user is supplied with a plurality of injection devices 10 they can be loaded into the packaging assembly 100. The lid 120 is moved into the open position and each of the injection devices 10 is inserted into a corresponding one of the openings 151. The lid 120 is moved into the closed position. The packaging assembly 100 is placed in the fridge until the first scheduled dosing time is due. The packaging assembly 100 may be placed in the fridge before or after the initial insertion of injection devices 10.

For example, a dosing time for one type of injection device 10 may be scheduled every 14 days or 28 days, according to the prescription and/or product patient leaflet of the medicament provided with the injection device 10. For some injection devices 10, a period of time between scheduled dosing times may be between 2 days and 60 days, according to the requirements of the medicament. The packaging assembly 100 may be configured to contain and store injection devices 10 of multiple types, simultaneously or at different points in time. The packaging assembly 100 may contain a plurality of injection devices 10 providing one or more different medicaments with one or more different dosing intervals.

The packaging assembly 100 is configured to establish communication with one or more external devices 300. The packaging assembly 100 is configured to determine whether or not the fridge door is open, and to establish communication conditional on the fridge door being open. The packaging assembly 100 is further configured to transmit information relating to the plurality of injection devices 10 to an external device 300. The packaging assembly 100 may be configured to request information relating to the plurality of injection devices from an external device 300.

The packaging assembly 100 is further configured to provide the user with a visual and/or audio reminder when the scheduled dosing time is due. The packaging assembly 100 may be further configured to provide the reminder conditional on the fridge door being open. The packaging assembly 100 may be further configured to determine whether the lid 120 is in the open position or the closed position, and to deactivate the audio reminder upon detection of the lid 120 being moved to the open position.

Figure 2A:
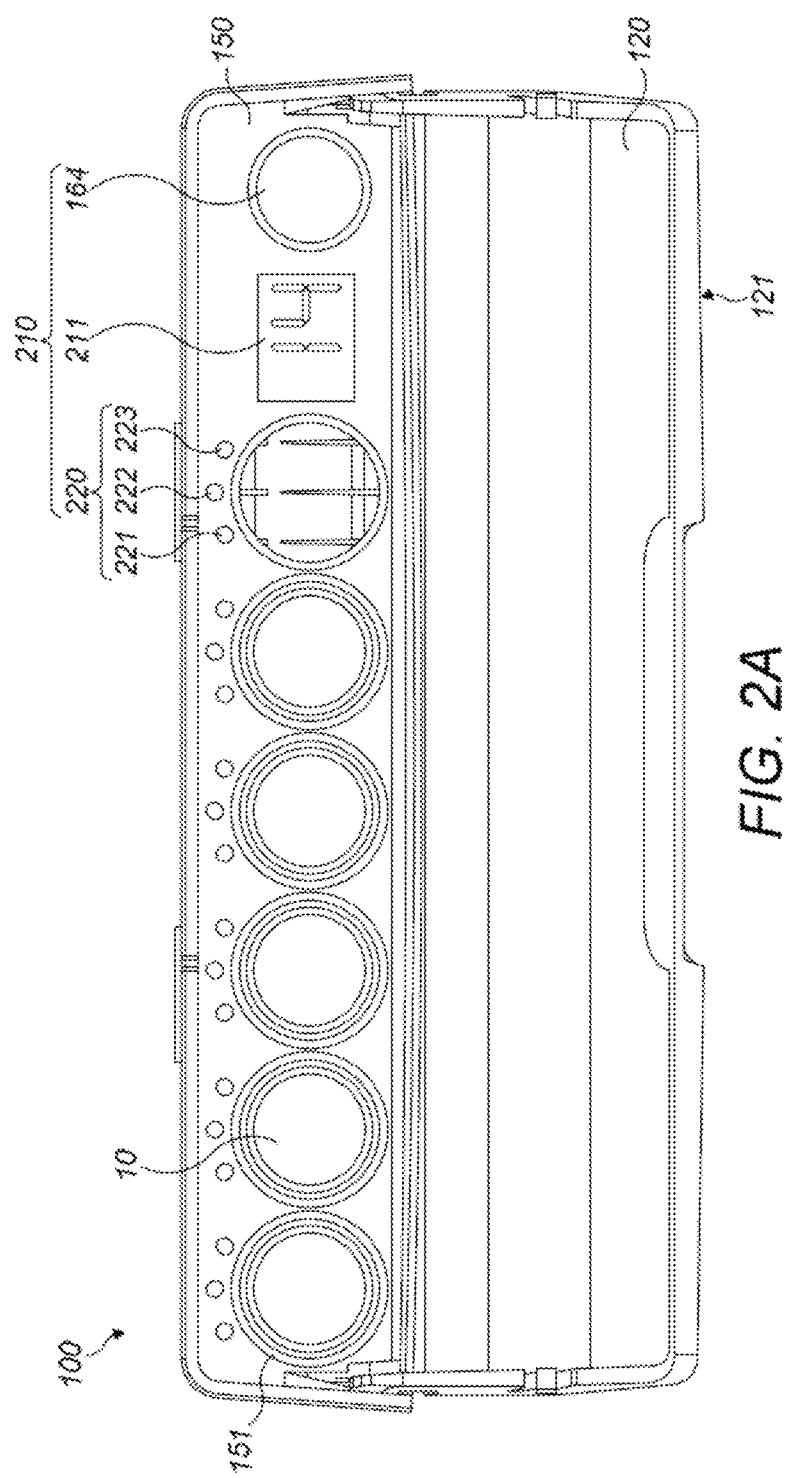
FIG. 2A is a front projection view of the packaging assembly of FIG. 1.

FIG. 2A shows the packaging assembly 100 from the front with the lid 120 in the open position. The panel 150 and openings 151 are visible. The packaging assembly 100 as shown contains a plurality of injection devices 10, each of which may be of a different device type. Different types of injection device 10 may provide different medicaments. Alternatively, different types of injection device 10 may have different dosages or concentrations of the same medicament, or different methods of delivering the medicament. Different types of injection device 10 may have different dosing intervals.

Figure 3:
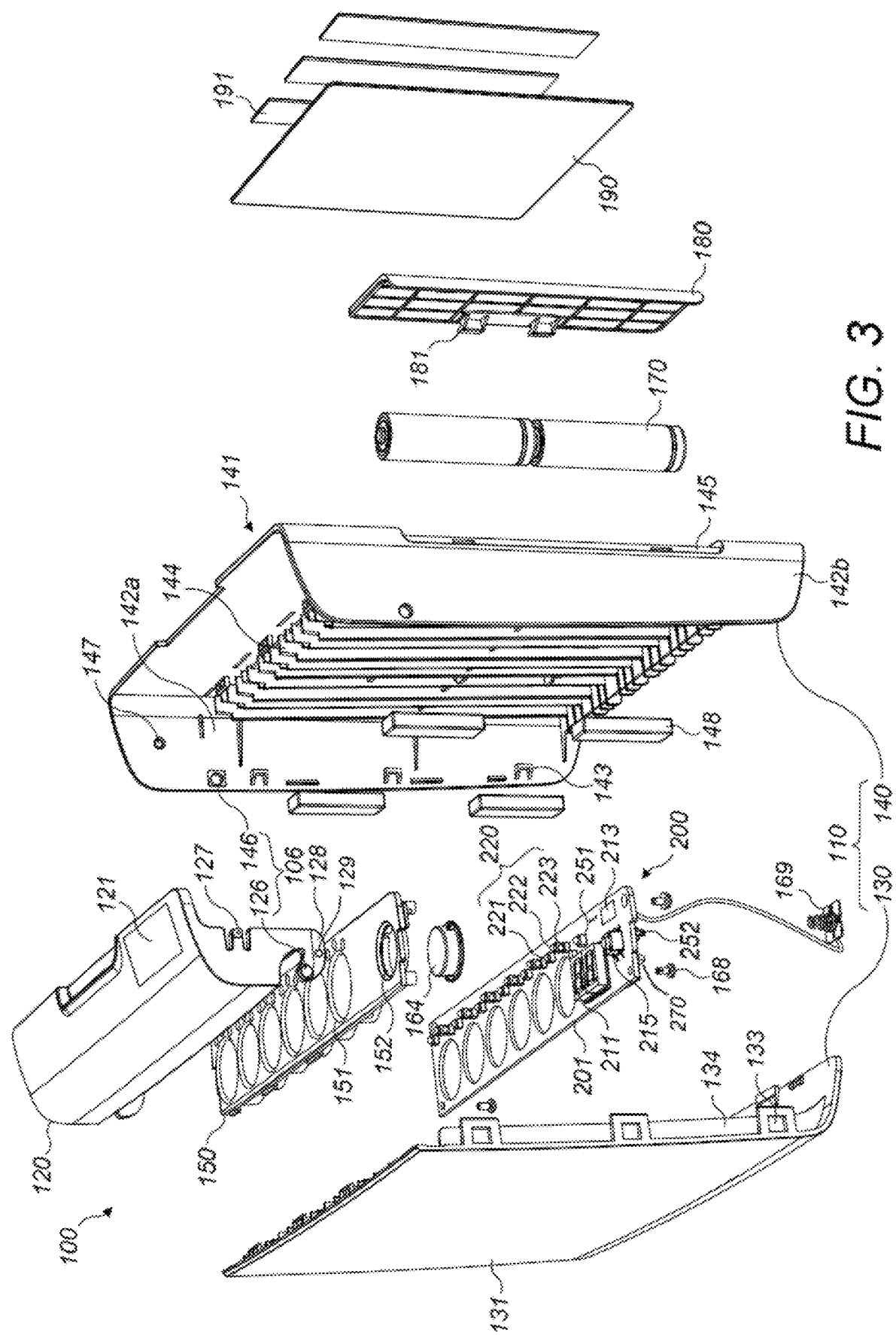
FIG. 3 is an exploded view of the packaging assembly of FIG. 1.

The packaging assembly 100 includes an electronics system 200 (see, e.g., FIG. 3). The electronics system 200 comprises multiple components that are connected together to provide a specific set of functions, described below. The components of the electronics system 200 are mounted on a printed circuit board (PCB 201), although instead they may be interconnected through some other medium.

The electronics system 200 is attached to the panel 150. Some of the electronic components of the electronics system 200 are user interface hardware components and together provide a user interface 210 for the packaging assembly 100.

The electronics system 200 comprises a display 211. The display 211 is an example of an optical transducer. The display 211 comprises two seven-segment light-emitting diode (LED) arrays. The display 211 is visible to the user through the transparent viewing window 121 in the lid 120. The electronics system 200 comprises a light-emitting diode (LED) array 220. The LED array 220 is an example of an optical transducer. The electronics system 200 comprises a reset button 164. The reset button 164 is an example of an input device. The reset button 164 is a sprung plunger button which may be depressed by the user. The electronics system 200 comprises a speaker 213 (see, e.g., FIG. 3). The speaker 213 is an example of an audio transducer.

The LED array 220 comprises an array of eighteen light-emitting diodes (LEDs). The LEDs of the LED array 220 are arranged on the panel 150, in proximity to the openings 151. The LED array 220 comprises three LEDs 221,222,223 for each of the six openings 151. Each of the three LEDs 221,222,223 can be illuminated with a different colour. For example, the LED array 220 may comprise a blue LED 221, a white LED 222 and a red LED 223 for each opening 151.

Figure 2B:
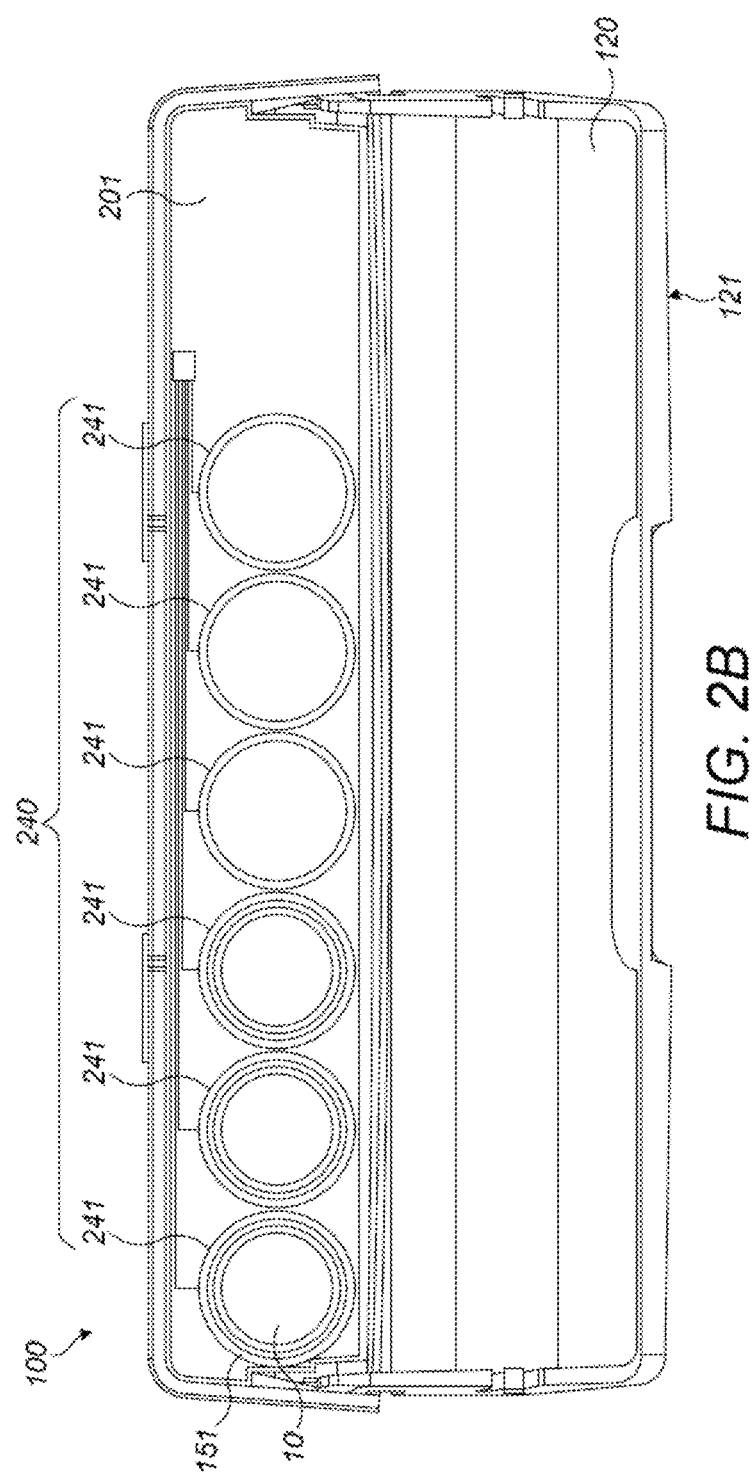
FIG. 2B is a front projection view of the packaging assembly of FIG. 1.

FIG. 2B shows an internal view of the packaging assembly 100 from the front. The rear face of the PCB 201 is illustrated.

The electronics system 200 comprises a sensor array 240. The sensor array 240 is mounted on a rear face of the PCB 201. The sensor array 240 comprises a plurality of device sensors 241. The number of device sensors 241 corresponds to the number of injection devices 10 which can be stored by the packaging assembly 100. Each device sensor 241 is mounted in proximity to one of the plurality of openings 151.

The device sensor 241 is configured to output a signal when an injection device 10 is located in the opening or during insertion into opening 151. The device sensor 241 is a radio-frequency identification (RFID) reader comprising a radio-frequency antenna. Each device sensor 241 is in the form of a loop corresponding to each of the openings 151. The device sensor 241 is arranged to detect a device tag 30 arranged on the injection device 10. The device tag 30 is a passive RFID tag comprising a radio-frequency antenna. The device sensor 241 generates an electromagnetic field, which activates the device tag 30, and detects a response signal transmitted by the device tag 30. The device sensor 241 may be configured to read device information stored on the device tag 30. The processor arrangement 230 may store device information received from an injection device 10.

The sensor array 240 may include electronic components that are separate to the device sensors 241 but form part of the sensor array 240 itself. The device sensors 241 may provide signals transmitted by a device tag 30 and the electronic components perform analysis of the signal and communication to the processor arrangement 230. Alternatively, each device sensor 241 may include electronic components to perform analysis of a detected signal. Further alternatively, the analysis of incoming signals may be performed by the processor arrangement 230.

Figure 5:
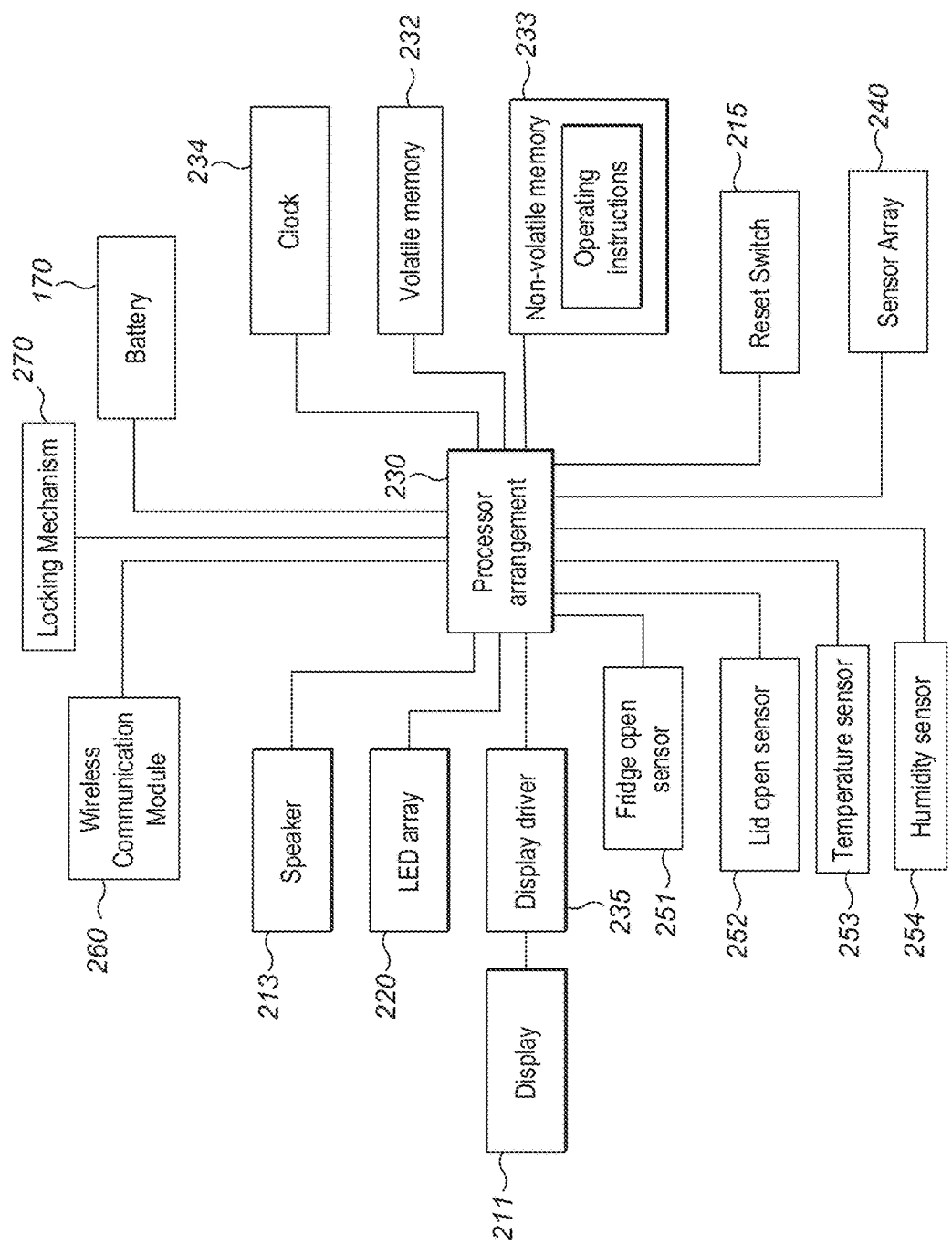
FIG. 5 is a block diagram of an electronics system of the packaging assembly, according to an exemplary embodiment.

The electronics system 200 is shown schematically in FIG. 5. The electronics system 200 comprises a processor arrangement 230. The processor arrangement 230 controls operation of the other hardware components of the electronics system 200. The processor arrangement 230 is configured to control the hardware components which form the user interface 210. The processor arrangement 230 is configured to process one or more input signals from at least one input sensor.

With reference to FIG. 3, an exploded view of the packaging assembly 100 according to the first embodiment is shown. The case 110 of the packaging assembly 100 comprises a first part 130 and a second part 140. The first part 130 of the case 110 is formed from a single piece. The first part 130 of the case 110 comprises the lower face 131 and the base of the packaging assembly 100. Along each side edge of the lower face 131, a plurality of openings 133 are formed for engaging with the second part 140 of the case 110. Three openings 133 are formed along each edge of the first part 130. The first part 130 further comprises a plurality of dividers 134 for holding the plurality of injection devices 10 (see, e.g., FIG. 1) in position within the case 110.

The second part 140 comprises the upper face 141, a first side wall 142a and a second side wall 142b of the case 110. The second part 140 is formed from a single piece. The second part 140 further comprises a plurality of dividers 144 for holding and storing the plurality of injection devices 10 in position within the case 110. The dividers 144 of the second part 140 are aligned with the dividers 134 of the first part 130.

The case 110 of the packaging assembly 100 comprises a plurality of magnets 148. The magnets 148 are fixed in position on an internal side of the upper face 141. The case comprises four magnets 148 fixed in a square arrangement. The plurality of magnets 148 allows the upper face 141 of the case 110 to be releasably attached to a magnetic surface, for example, a steel surface. The magnets 148 may be neodymium magnets.

The packaging assembly 100 further comprises a mounting plate 190. The mounting plate 190 comprises a plurality of adhesive strips 191. The mounting plate 190 can be fixed to a surface using the adhesive strips 191, such as, for example, a wall or under a shelf within a fridge. The mounting plate 190 is formed from a magnetic material, for example, steel. The case 110 can be releasable attached to the surface by magnetically attaching to the beforehand fixed mounting plate 190.

The mounting plate 190 comprises three adhesive strips 191. The adhesive strips 191 are arranged in parallel across the width of the mounting plate 190 and each adhesive strip 191 extends along substantially the full length of the mounting plate. Alternatively, the mounting plate 190 may comprise only two adhesive strips 191 which are spaced apart on the mounting plate 190, or may comprise more than three adhesive strips 191 extending in parallel. Further alternatively, the mounting plate 190 may comprise four adhesive strips 191 positioned in a rectangular arrangement, for example, at each corner of the mounting plate 190. The mounting plate may comprise any number of adhesive strips 191 arranged in a regular array.

The mounting plate 190 may alternatively be placed, without adhesive, on an upper side of a shelf. The case 110 may be magnetically held beneath the shelf through a magnetic attraction to the mounting plate 190.

The packaging assembly 100 further comprises a plurality of batteries 170. The batteries 170 are arranged to provide power to the components of the electronics system 200, including the user interface 210. The second part 140 of the case 110 comprises a battery opening 145 formed in the upper face 141. The battery opening 145 is configured to receive the plurality of batteries 170. A battery cover 180 is configured to slidably engage with the battery opening 145 of the second part 140 and to cover the battery opening 145 when the packaging assembly 100 is in use. The battery cover 180 comprises a plurality of latches 181 arranged to engage with the second part 140 of the case 110.

Each of the first side wall 142a and the second side wall 142b of the case 110 comprises a plurality of engaging hooks 143. The engaging hooks 143 are arranged on an inner face of the respective side wall. Each of the side walls 142 comprises three engaging hooks 143. The engaging hooks 143 are each configured to engage with the corresponding opening 133 in the first part 130 of the case 110. Each of the side walls 142 comprises a first hinging part 146. Each of the side walls 142 comprises a first latching part 147.

The lid 120 of the case 110 comprises a second hinging part 126 configured to engage with the first hinging part 146 of the second part 140 of the case 110. The first hinging part 146 and the second hinging part 126 together form a hinge 106 for attaching the lid 120 to the second part 140 of the case 110. For example, the first hinging part 146 comprises an opening and the second hinging part 126 comprises a protrusion arranged to fit within the opening of the first hinging part 146. The second hinging part 126 is configured to rotate within the opening of the first hinging part 146.

The lid 120 of the case 110 comprises a second latching part 127 configured to engage with the first latching part 147 of the second part 140 of the case 110. The second latching part 127 is configured to releasably engage with the first latching part 147 to maintain the lid 120 in a closed position. For example, the first latching part 147 comprises an opening and the second latching part 127 comprises a protrusion configured to releasably engage with the opening of the first latching part 147.

The lid 120 is formed from a translucent plastic material. A portion of the lid 120 is clear and transparent to form a viewing window 121 through the lid 120.

The panel 150 is held in position between the first part 130 and the second part 140 of the case 110. The panel 150 comprises the plurality of openings 151. The openings 151 are configured to hold the corresponding plurality of injection devices 10. The panel 150 further comprises one or more openings 152 for the hardware components of the user interface 210.

The packaging assembly 100 comprises the electronics system 200. The electronics system 200 includes the hardware components of the user interface 210, namely the display 211, the LED array 220, the speaker 213 and the reset button 164. The display 211 of the user interface 210 is visible through the transparent viewing window 121 of the lid 120.

A plurality of screws 168 are arranged to attach a support of the electronics system 200, for instance a PCB 201, to a rear face of the panel 150. The sensor array 240 is mounted on the rear face of the PCB 201. Alternatively, the sensor array 240 may be arranged on the front face of the PCB 201. Further alternatively, the sensor array 240 may be arranged on the rear face of the panel 150. The electronics system 200 is coupled with a battery contact 169. The battery contact 169 is mounted with the plurality of batteries 170 to supply power to the electronics system 200.

The electronics system 200 comprises a reset switch 215. The reset button 164 is a sprung plunger button arranged to be pushed by the user. The reset switch 215 is a mechanical switch mounted on the electronics system 200. The reset switch 215 is positioned below the reset button 164. The reset switch 215 is arranged to be actuated by the reset button 164. The reset button 164 may be coupled to the reset switch 215.

The electronics system 200 comprises a light sensor 251. The light sensor 251 is mounted on the PCB 201 of the electronics system 200. The light sensor 251 comprises a phototransistor configured to pass a current according to the amount or intensity of light which is incident on the light sensor 251. The light sensor 251 is an example of a fridge open sensor.

The light sensor 251 may be of the type where the inherent device characteristics are such that an intensity of light exceeding a threshold results in a signal of one type (e.g. high) and an intensity of light below the threshold results in a signal of an opposite type (e.g. low). Alternatively, comparison of the intensity to a threshold may be performed by electronic components that are separate to the device of the light sensor 251 but form part of the light sensor itself. Here, the light sensitive device provides a signal with a level that varies according to the detected light intensity and the electronic components perform analysis of the signal compared to a threshold.

Further alternatively, the comparison may be performed in the digital domain by the processor arrangement 230. Here, the light sensor provides a signal with a level that varies according to the detected light intensity, this is converted by an analogue to digital converter (if not already a digital signal) and the processor arrangement compares the signal to a threshold. Unless the threshold is inherent in the device, the threshold may be preset (that is, predetermined and set at the design or manufacture stage) or it may be dynamically adjustable having regard to operating conditions.

The arrangement may be configured to filter out short duration bursts of light exceeding the threshold, which filtering may occur through the use of slow response components, so as to reduce the occurrence of false triggering. As will be appreciated, if there is false triggering from short duration periods of light intensity exceeding the threshold, the result is short duration activation of user interface 210 components.

The electronics system 200 comprises a hinge switch 252. The hinge switch 252 may be an electro-mechanical switch such as a microswitch or other miniature snap action switch. The hinge switch 252 is an example of a lid open sensor.

The hinge switch 252 is arranged to engage with the lid 120 of the case 110 when the lid 120 is in a closed position. An actuating part 128 of the lid 120 is shaped so as to press the hinge switch 252 when the lid 120 is in a closed position. The hinge switch 252 is mounted at an edge of the PCB 201 of the electronics system 200. The actuating part 128 of the lid 120 is arranged to pass the edge of the PCB 201 of the electronics system 200 when the lid 120 is in a closed position.

The hole 129 is provided in the actuating part 128 of the lid 120, the hole 129 is provided so that after the actuation of a corresponding mechanism the lid 120 is locked in place.

The locking mechanism 270 is positioned so as to engage with the corresponding hole 129. The locking mechanism may be that of a solenoid actuator. When the actuator is engaged, the lid 120 will be locked in position. The locking mechanism 270 is not limited to being a solenoid actuator, other embodiments may utilise different mechanisms for locking the lid 120 in position.

The electronics system 200 may further comprise one or both of a temperature sensor 253 and a humidity sensor 254 (see, e.g., FIG. 5).

The electronics system 200 further comprises a processor arrangement 230 (see, e.g., FIG. 5). The processor arrangement 230 is configured to process the input signals from the one or more sensors and the switches on the electronics system 200. The processor arrangement 230 is configured to control the outputs of the user interface 210 elements on the electronics system 200.

The electronics system 200 further comprises a wireless communication module 260 (see, e.g., FIG. 5). The wireless communication module 260 is configured to communicate wirelessly with one or more devices external to the packaging assembly 100, under the control of the processor arrangement 230. The wireless communication module 260 may be configured to establish communication using a short range communication protocol such as Bluetooth, ZigBee, Infra-red Data Association (IrDA) or similar, using a wireless local area network (LAN) such as a Wi-Fi or Li-Fi network, or using a mobile communication protocol such as GSM, CDMA, EDGE, GPRS, HSPA, WiMAX, LTE or similar.

The wireless communication module 260 is configured to transmit signals from the processor arrangement 230 to the one or more external devices 300. The wireless communication module 260 is configured to receive signals transmitted by the one or more external devices 300. Transmitted signals may be encrypted or otherwise protected to ensure data privacy and data integrity. A pairing process may be required between the wireless communication module 260 and each of the one or more external devices 300 to establish an authorised wireless communication.

Figure 4:
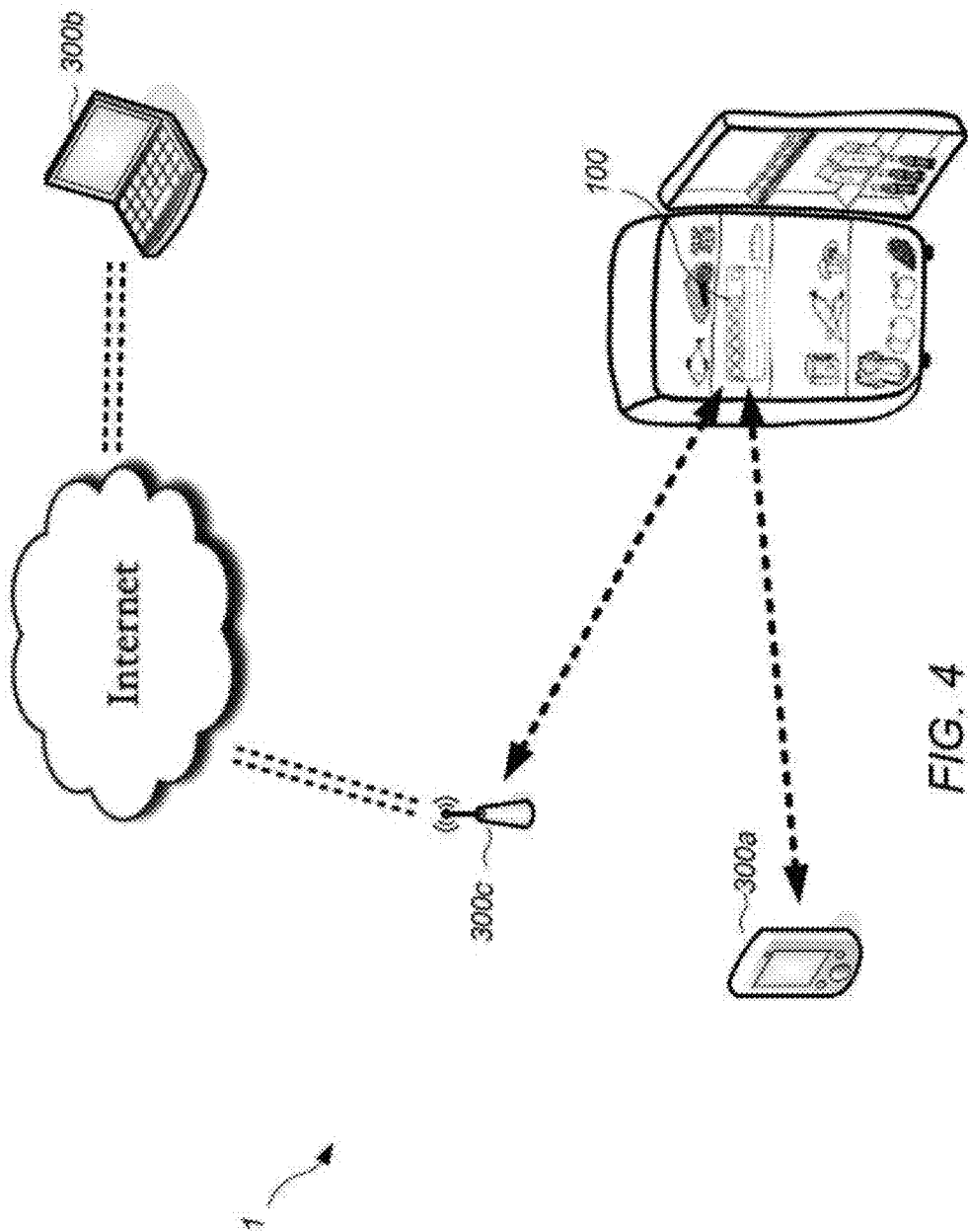
FIG. 4 is a system diagram of the packaging assembly of FIG. 1 in an exemplary operating environment.

With reference to FIG. 4, a system 1 according to an embodiment is shown. The system 1 comprises the packaging assembly 100. The packaging assembly 100 is shown to be located in a refrigerator, according to an exemplary mode of operation. The packaging assembly 100 may be placed in the refrigerator by a user, and a plurality of injection devices 10 may be placed in the packaging assembly 100.

The system further comprises a plurality of devices 300 external to the packaging assembly 100. The system comprises a first external device 300*a*, a second external device 300*b* and a wireless terminal 300*c*.

The first external device 300*a* may be a mobile phone. The first external device 300*a* is an example of a wireless communication device. The first external device 300*a* is configured to communicate wirelessly using a wireless communication protocol. For example, the first external device may communicate wirelessly using Wi-Fi, Bluetooth, ZigBee, IrDA or similar.

The first external device 300*a* is an example of a user device. The first external device 300*a* can be operated by, for example, a patient. According to the exemplary mode of operation, the first external device 300*a* is in close proximity with the packaging assembly 100. For example, the first external device 300*a* may be carried or held by the patient when the refrigerator is opened.

The second external device 300*b* may be a personal computer. The second external device 300*b* is an example of an internet connected device. The second external device 300*b* is connected to the internet through a wired connection or a wireless connection. For example, the second external device 300*b* is connected to the internet through an Ethernet connection, a power-line communication (PLC) connection or wirelessly using Wi-Fi, Li-Fi or a mobile communication protocol such as GSM, CDMA, EDGE, GPRS, HSPA, WiMAX, LTE or similar.

The second external device 300*b* is an example of a user device. The second external device 300*b* can be operated by, for example, a caregiver or a parent/guardian of the patient.

According to the exemplary mode of operation, the second external device 300*b* is at a remote location from the packaging assembly 100. The second external device 300*b* is an example of a remote device. For example, the second external device 300b is located at a place of work or residence of the caregiver which is remote from the residence of the patient.

The wireless terminal 300c may be a wireless access point such as a wireless router. The wireless terminal 300c is configured to broadcast a Wi-Fi signal. Alternatively, the wireless terminal 300c may be configured to broadcast a signal using Li-Fi or any alternative wireless protocol. The wireless terminal 300c provides access to a wireless LAN for compatible devices within range. The wireless terminal 300c may be configured further to provide access to the Internet through the wireless LAN. The wireless terminal 300c is connected to the internet through an Ethernet connection, a PLC connection or wirelessly using Wi-Fi, Li-Fi or a mobile communication protocol such as GSM, CDMA, EDGE, GPRS, HSPA, WiMAX, LTE or similar.

The packaging assembly 100 is configured to establish communication with one or more of the plurality of external devices 300. The packaging assembly 100 is configured to establish communication conditional on the fridge door being open. The wireless communication module 260 is configured to broadcast a connection request signal when the fridge door is determined to be open. If a response signal is received from one of plurality of external devices 300, the wireless communication module 260 is configured to establish communication with the external device 300. The processor arrangement 230 controls communication with the connected external device 300, according to the type of external device 300.

When communication is established with the first external device 300a, the processor arrangement 230 determines that the wireless communication module 260 is connected with a user device. The processor arrangement 230 can control the wireless communication module 260 to transmit information relating to the plurality of injection devices 10 to the first external device 300a. The wireless communication module 260 may transmit a status of the injection devices 10, for example, the wireless communication module 260 may transmit an alert to the first external device 300a if a scheduled dosing time is due, or may transmit the time remaining until the next scheduled dosing time is due. The wireless communication module 260 may transmit device information received from the sensor array 240, for example, the wireless communication module 260 may transmit the number and types of injection devices 10 stored in the packaging assembly 100. The wireless communication module 260 may transmit an alert to the first external device 300a if one of the injection devices 10 has expired.

The wireless communication module 260 may transmit injection information to the first external device 300a if a scheduled dosing time is due. For example, the wireless communication module 260 may transmit a warm-up time period to the first external device 300a, representing the recommended period of time to wait before injection to allow the injection device 10 to reach room temperature. In this way, the fridge may be closed and the first external device 300a may be used to monitor the warm-up time period. The warm-up time period may be fixed or may depend on the type of injection device 10. The warm-up time period for an injection device 10 may be stored in the non-volatile memory 233 or may be received by the device sensor 241 from the injection device 10.

Injection information transmitted by the wireless communication module 260 to the first external device 300a may include instructions for the use of the injection device 10. Instructions may be transmitted in the form of text, diagrams or audio or video instructions. Instructions for the use of each injection device 10 may be stored in the non-volatile memory 233 or may be received by the device sensor 241 from the injection device 10. Alternatively, the wireless communication module 260 may transmit the ID or the device type of the injection device 10 to the first external device 300a, and the first external device 300a may retrieve the instructions for injection from an external database e.g. via the internet.

The wireless communication module 260 may transmit status information of the packaging assembly 100 to the first external device 300a. For example, the wireless communication module 260 may transmit environmental information provided by the temperature sensor 253 or the humidity sensor 254. Alternatively, the wireless communication module 260 may transmit a status alert to the first external device 300a when the status of the packaging assembly 100 is abnormal, for example, when the detected temperature or humidity is too high.

If the first external device 300a is not in range, the wireless communication module 260 may transmit information to the first external device 300a through an internet connection, as will be described below with respect to the second external device 300b and the third external device 300c. The wireless communication module 260 may transmit information indicating an abnormal status of the packaging assembly 100 to the first external device 300a through the internet or wireless LAN. The wireless communication module 260 may transmit an alert through the internet or wireless LAN if the first external device 300a is moved beyond the range of direct short-range communication while the fridge door is open. For example, if a Bluetooth connection between the wireless communication module 260 and the first external device 300a is lost while the fridge door is open, the processor arrangement 230 may determine that the user of the first external device 300a has moved out of range and has left the fridge door open, and will operate the wireless communication module 260 to transmit an alert to the first external device 300a.

The wireless communication module 260 may be configured further to request information from the first external device 300a. The wireless communication module 260 may request a user identity from the first external device 300a. The wireless communication module 260 provides the received user ID to the processor arrangement 230. The processor arrangement 230 may be configured to activate the user interface 210 conditional on the reception of a recognized user ID by the wireless communication module 260. A list of one or more recognized user devices may be stored in the non-volatile memory 233. The processor arrangement 230 may operate the LED array 220 to indicate a particular injection device 10, according to the identified user. In this way, the packaging assembly 100 may store different injection devices 10 for a plurality of different users. The processor arrangement 230 may be configured further to unlock a locking mechanism 270 on the lid 120 of the case 110, conditional on the reception of a recognized user ID by the wireless communication module 260.

When communication is established with the wireless terminal 300c, the processor arrangement 230 determines that the wireless communication module 260 is connected with a wireless access point. The processor arrangement 230 controls the wireless communication module 260 to access the wireless LAN of the wireless terminal 300c. The wireless communication module 260 may establish communication with one or more external devices 300 through the wireless LAN of the wireless terminal 300c. For example, the wireless communication module 260 may communicate with the first external device 300a through the wireless LAN if the first external device 300a is beyond the range of direct short-range communication from the wireless communication module 260.

The processor arrangement 230 controls the wireless communication module 260 further to establish a connection to the internet through the wireless terminal 300c. When an internet connection is established, the processor arrangement 230 controls the wireless communication module 260 to establish communication with one or more external devices 300 through the internet. A list of external devices 300 may be stored in the non-volatile memory 233 with network address information used to establish communication through the internet. Network address information may include, for example, an internet protocol (IP) address, a uniform resource indicator (URI) or uniform resource location (URL) of the external device 300.

The wireless communication module 260 may establish a connection with the second external device 300b through the internet. The wireless communication module 260 may transmit an alert to the second external device 300b if a scheduled dosing time is due, or may transmit the time remaining until the next scheduled dosing time is due. The wireless communication module 260 may further transmit the number and types of injection devices 10 stored in the packaging assembly 100. The wireless communication module 260 may transmit an alert to the second external device 300b if one of the injection devices 10 has expired.

The wireless communication module 260 may transmit status information of the packaging assembly 100 to the second external device 300b. For example, the wireless communication module 260 may transmit environmental information provided by the temperature sensor 253 or the humidity sensor 254. Alternatively, the wireless communication module 260 may transmit a status alert to the second external device 300b when the status of the packaging assembly 100 is abnormal, for example, when the detected temperature or humidity is too high. The wireless communication module 260 may transmit an alert signal to the second external device 300b if the fridge door has been left open. The processor arrangement 230 may determine if the fridge door has been open for e.g. more than 5 minutes, and may operate the wireless communication module 260 to transmit an alert signal to the second external device 300b.

The wireless communication module 260 may transmit status information allowing the user of the second external device 300b, for example a parent/guardian or caregiver of the patient, to monitor the use of the packaging assembly 100. The wireless communication module 260 may transmit a status update to the second external device 300b when the fridge door is opened and closed. The wireless communication module 260 may transmit a status update to the second external device 300b when the lid 120 is opened and closed. The wireless communication module 260 may transmit a status update when the sensor array 240 detects the removal of an injection device 10 from the packaging assembly 100. In this way, the packaging assembly 100 allows a caregiver to remotely monitor the patient's compliance with the dosing schedule.

With respect to FIG. 5, a schematic representation of the electronics system 200 of the packaging assembly 100 according to the first embodiment is shown. The electronics system 200 comprises the processor arrangement 230. The processor arrangement 230 and other hardware components may be connected via a system bus. Each hardware component may be connected to the system bus either directly or via an interface. One or more batteries 170 are arranged to provide power to the electronics system 200.

The processor arrangement 230 controls operation of the other hardware components of the electronics system 200. The processor arrangement 230 may be an integrated circuit of any kind. The processor arrangement 230 may for instance be a general purpose processor. It may be a single core device or a multiple core device. The processor arrangement 230 may be a central processing unit (CPU) or a general processing unit (GPU). Alternatively, it may be a more specialist unit, for instance a RISC processor or programmable hardware with embedded firmware. Multiple processors may be included. The processor arrangement 230 may be termed processing means.

The processor arrangement 230 has an internal processing clock speed of about 4 MHz. The processor arrangement 230 also has a stand-by clock speed of 2 Hz to reduce energy consumption. The internal processing clock speed and stand-by clock speed are selected to provide a balance between power usage and usability. A greater clock speed provides improved usability by reducing the time required for the processor arrangement 230 to respond to an input. However, a greater clock speed will increase the power usage of the processor arrangement 230. The stand-by clock speed may be selected between 0.5 and 100 Hz.

The electronics system 200 comprises a working or volatile memory 232. The processor arrangement 230 may access the volatile memory 232 to process data and may control the storage of data in memory. The volatile memory 232 may be a RAM of any type, for example Static RAM (SRAM), Dynamic RAM (DRAM), or it may be Flash memory. Multiple volatile memories may be included, but are omitted from the Figure.

The electronics system 200 comprises a non-volatile memory 233. The non-volatile memory 233 stores a set of operation instructions for controlling the normal operation of the processor arrangement 230. The non-volatile memory 233 may be a memory of any kind such as a Read Only Memory (ROM), a Flash memory or a magnetic drive memory. Other non-volatile memories may be included, but are omitted from the Figure.

The processor arrangement 230 operates under the control of the operating instructions. The operating instructions may comprise code (i.e. drivers) relating to the hardware components of the electronics system 200, as well as code relating to the basic operation of the packaging apparatus. The operating instructions may also cause activation of one or more software modules stored in the non-volatile memory 233. Generally speaking, the processor arrangement 230 executes one or more instructions of the operating instructions, which are stored permanently or semi-permanently in the non-volatile memory 233, using the volatile memory 232 temporarily to store data generated during execution of the operating instructions.

The processor arrangement 230, the volatile memory 232 and the non-volatile memory 233 may be provided as separate integrated circuit chips connected by an off-chip bus, or they may be provided on a single integrated circuit chip. The processor arrangement 230, the volatile memory 232 and the non-volatile memory 233 may be provided as a microcontroller.

The electronics system 200 comprises a clock 234. The clock 234 may be a clock crystal, for example, a quartz crystal oscillator. The clock 234 may be a separate component to the processor arrangement 230 which is configured to provide a clock signal to the processor arrangement 230. The processor arrangement 230 may be configured to provide a real time clock based on the signal from the clock 234. Alternatively, the clock 234 may be a clock crystal which is provide on a single integrated circuit chip with the processor arrangement 230.

The processor arrangement 230 is configured to perform at least one countdown operation. The processor arrangement 230 may perform a different countdown operation for each different type of injection device 10 stored in the packaging assembly 100. The processor arrangement 230 monitors the one or more countdown operations to determine the number of days remaining until the next scheduled dosing time. Countdown operations are set and activated in response to the insertion of an injection device 10 into one of the openings 151, detected by the sensor array 240. The processor arrangement 230 records the number of days for each countdown timer to the volatile memory 232 and every 24 hours reduces the recorded number of days by one.

The predetermined time period for each countdown to the next scheduled dosing time may be different for each different type of device. For example, if a time period until the next scheduled dosing time is due is 14 days for a certain type of device, the countdown timer for that type of device is started from 14 days. If a time period until the next scheduled dosing time is due is 28 days for another type of device, the countdown timer for that type of device is started from 28 days.

Every 24 hours, the number of days recorded to the volatile memory 232 is reduced by one. The processor arrangement 230 monitors the lowest active countdown to determine the number of days remaining until the next scheduled dosing time. When 1 day remains until the next scheduled dosing time, the processor arrangement 230 may control the electronics system 200 to generate an output to indicate that the next scheduled dosing time is near. On the day of the scheduled dosing time, the processor arrangement 230 may control the electronics system 200 to generate an output to indicate that the next scheduled dosing time is due. The hardware components of the electronics system 200 which form the user interface 210 may be controlled to indicate that the next scheduled dosing time is due. The user interface 210 may by controlled to indicate that the next scheduled dosing time is due for a certain device type, or for the injection device 10 stored in a certain opening 151.

On one day, for instance the first or last day, the reduction of the number of days may be provided in less than 24 hours. For instance, it may be achieved in 20 hours or 22 hours. This can help to prevent creep of the alert time to later and later in the day after multiple resets of the countdown timer. Alternatively, when the remaining number of days recorded in the volatile memory is equal to one, the processor arrangement 230 may be configured to reduce the time remaining until the next scheduled dosing time is due. For example, the processor arrangement 230 may be configured to wait only 23 hours before reducing the number of days to zero. In this way, the time of day at which the scheduled dosing time becomes due is one hour earlier than the time at which the reset button 164 was pressed.

The processor arrangement 230 may be configured to perform one or more timing operations. For example, the processor arrangement 230 may operate a door timer to monitor the amount of time that the door of the fridge has been open. The processor arrangement 230 may operate a reset timer to monitor the amount of time that the reset button 164 has been pressed. The processor arrangement 230 may start a timing operation from zero and monitor an increasing amount of time. Alternatively, the processor arrangement 230 may start a timing operation from a predetermined time and count down until the timer expires.

The processor arrangement 230 may be configured to provide a current date and time based on the signal from the clock 234. The processor arrangement 230 may monitor the expiry date for each injection device 10 stored in the packaging assembly 100. The processor arrangement 230 may determine that an injection device 10 has expired when the expiry date is in the past. The processor arrangement 230 may control the electronics system 200 to generate an output to indicate that an injection device 10 has expired.

The processor arrangement 230 may be configured to check the state of charge of one or more batteries 170 included in the packaging assembly 100. The state of charge is determined to be low if it is below a threshold (which may be built into the design of the packaging arrangement). The state of charge may be determined by measurement of the voltage provided by the battery 170, by monitoring energy use from a full state of charge, or a combination of these two techniques.

The electronics system 200 comprises a fridge open sensor 251. The fridge open sensor 251 may be a light sensor, for example a phototransistor, mounted on the PCB 201. The fridge open sensor 251 is configured to provide a signal to the processor arrangement 230 when light is incident on the phototransistor. For example, when the packaging assembly 100 is stored within a fridge, the fridge open sensor 251 may provide an indication that a door of the fridge is open by providing a signal when ambient light from outside the fridge, or light from an internal fridge light, is incident on the phototransistor. When the fridge door is closed, no light is incident on the phototransistor and the fridge open sensor 251 provides no signal or a small signal.

The fridge open sensor 251 may comprise a phototransistor configured to pass a current according to the amount or intensity of light which is incident on the phototransistor. The fridge open sensor 251 may be configured to provide a signal of one type (e.g. high) when an intensity of incident light exceeds a threshold, and a signal of an opposite type (e.g. low) when an intensity of incident light is below the threshold.

Alternatively, the fridge open sensor 251 provides a current signal to the processor arrangement 230 according to the intensity of light which is incident on the phototransistor. The received signal may be compared to a threshold by the processor arrangement 230. The threshold may be a preset threshold stored in the non-volatile memory 233, or it may be dynamically adjustable having regard to operating conditions.

The processor arrangement 230 is configured to determine whether a door of a fridge in which the packaging assembly 100 is stored is open or closed, based on a signal received from the fridge open sensor 251.

The processor arrangement 230 is configured to start a door timer when the fridge door is opened. The processor arrangement 230 starts the door open timer in response to a signal from the light sensor 251 to indicate that the fridge door is open. The signal from the light sensor 251 may be used to trigger an interrupt port input to the processor arrangement 230. After the timer has been started, the device can be said to be in a door open state. When the fridge door is closed, the device can be said to be in a door closed state.

The processor arrangement 230 may be configured to enter a partial sleep state when the time period measured by the door timer is over a threshold time. For example, the processor arrangement 230 may enter a partial sleep state when the fridge door has been open for 5 minutes. The door open timer may be configured to expire after a predetermined time, for instance in the range of 1 minute to 10 minutes. The processor arrangement 230 may control the electronics system 200 not to generate an output in the partial sleep state. In the door closed state and in the partial sleep state, the processor arrangement 230 changes to the stand-by clock speed to reduce power usage.

The device transitions from the door open state to the partial sleep state when the door timer passes the 5 minutes mark. The wireless communication module 260 may be controlled to transmit an alert signal when the door timer passes the 5 minute mark. The door timer may be started at 5 minutes when the door is detected to be opened and count down such that the timer expires if the door is not closed within 5 minutes.

The electronics system 200 comprises a temperature sensor 253, such as a thermistor or thermocouple. The temperature sensor 253 may be mounted on the PCB 201. Alternatively, the temperature sensor 253 may be fixed in any position inside or outside the case 110 and connected to the processor arrangement 230 by a cable. The temperature sensor 253 may comprise a thermistor configured to pass a current according to the temperature within the packaging assembly 100. The temperature sensor 253 may be configured to provide a signal of one type (e.g. high) when an internal temperature of the packaging assembly 100 exceeds a threshold, and a signal of an opposite type (e.g. low) when the temperature is below the threshold.

Alternatively, the temperature sensor 253 provides a current signal to the processor arrangement 230 according to the internal temperature of the packaging assembly 100. The received signal may be compared to a threshold by the processor arrangement 230. The threshold may be a preset threshold stored in the non-volatile memory 233, or it may be dynamically adjustable having regard to operating conditions. The wireless communication module 260 may transmit an alert signal when the determined temperature exceeds the threshold, conditional on the fridge door being open.

The electronics system 200 comprises a humidity sensor 254, such as a humistor or a capacitive hygrometer. The humidity sensor 254 may be mounted on the PCB 201. Alternatively, the humidity sensor 254 may be fixed in any position inside or outside the case 110 and connected to the processor arrangement 230 by a cable. The humidity sensor 254 may comprise a humistor configured to pass a current according to the humidity within the packaging assembly 100. The humidity sensor 254 may be configured to provide a signal of one type (e.g. high) when an internal humidity of the packaging assembly 100 exceeds a threshold, and a signal of an opposite type (e.g. low) when the humidity is below the threshold.

Alternatively, the humidity sensor 254 provides a current signal to the processor arrangement 230 according to the internal humidity of the packaging assembly 100. The received signal may be compared to a threshold by the processor arrangement 230. The threshold may be a preset threshold stored in the non-volatile memory 233, or it may be dynamically adjustable having regard to operating conditions. The wireless communication module 260 may transmit an alert signal when the determined humidity exceeds the threshold, conditional on the fridge door being open.

The electronics system 200 comprises a sensor array 240. The sensor array 240 is arranged to detect one or more injection devices 10 inserted into or removed from the packaging assembly 100. The sensor array 240 is configured to detect whether or not an injection device 10 is moved through each of the openings 151. The sensor array 240 provides a signal to the processor arrangement 230 to indicate the presence of an injection device 10 in each of the openings 151. The processor arrangement 230 records in the volatile memory 232 whether or not an injection device 10 is stored in each of the openings 151. The processor arrangement 230 stores a device table in the volatile memory 232 which records whether or not an injection device 10 is stored in each of the openings 151.

The sensor array 240 comprises a plurality of device sensors 241. The number of device sensors 241 in the sensor array 240 corresponds to the number of injection devices 10 which can be stored in the packaging assembly 100. The sensor array 240 comprises one device sensor 241 for each of the openings 151.

A device sensor 241 comprises a radio-frequency (RF) antennae mounted in proximity to the corresponding opening 151. The processor arrangement 230 operates the device sensor 241 to transmit an RF electromagnetic signal through the antenna. When an injection device 10 is located at the opening 151, the electromagnetic signal activates a device tag 30 on the injection device 10. The device tag 30 comprises an RF antenna and a low power circuit. The device tag 30 is powered through induction by the RF signal broadcast by the device sensor 241.

The device tag 30 is arranged at a midpoint on the length of the injection device 10. The device tag 30 is activated when the midpoint of the injection device 10 passes through the opening 151. When activated, the device tag 30 transmits a response signal through the RF antenna. The device sensor 241 detects the response signal transmitted by the device tag 30 and provides a signal to the processor arrangement 230. The processor arrangement 230 determines whether the injection device 10 is being inserted into the opening 151 or removed from the opening 151, according to the information in the device table. The processor arrangement 230 updates the device table according to whether the injection device 10 is being inserted into the opening 151 or removed from the opening 151.

The device sensor 241 may receive device information from the device tag 30. The device tag 30 may comprise a non-volatile storage with stored device information. The device tag 30 may be configured to transmit the device information with the response signal when activated by the device sensor 241. The device tag 30 may store one or more of a device ID, a device type, an expiry date, a dosing time period and a warm-up time period for the injection device 10. The device sensor 241 may receive the device information transmitted with the response signal from the device tag 30. The device sensor 241 sends the received device information to the processor arrangement 230.

The sensor array 240 is operated by the processor arrangement 230 to scan for one or more injection devices 10 when the lid 120 is open and the packaging assembly 100 is in usual working mode. The processor arrangement 230 updates the device table based on device information received from the sensor array 240.

The processor arrangement 230 receives device information for each injection device 10 inserted into the packaging assembly 100. The processor arrangement 230 is configured to store received device information in the volatile memory 232. The received device information is stored in the volatile memory 232 in a device table.

The device ID represents a unique identifier for the injection device 10. Each injection device 10 has a unique device ID recorded on the device tag 30. The device type is related to the specific treatment provided by the injection device 10. The device type may be defined by any feature which differentiates injection devices 10 for different treatments. For example, the device type may be defined by one or more of the medicament contained in each injection device 10, the volume or concentration of the medicament and the method of administration. The device type may be represented by one field in the device table or, alternatively, may be represented by two or more distinct fields.

The device ID may be validated by the processor arrangement 230. The processor arrangement 230 may operate the user interface 210 to output a visual indication if a device ID is not recognised by the processor arrangement 230. The processor arrangement 230 may compare the device ID to a validation table stored in the non-volatile memory 233 or the volatile memory 232. The validation table may be pre-stored in the non-volatile memory 233 or the volatile memory 232. The validation table may be stored or updated through the wireless communication module 260. The validation table may be provided by an external device 300 through the wireless communication module 260. Alternatively, the device ID may be transmitted to an external device 300 and compared with a validation table stored in the external device 300. The user of the external device 300 may be any of, for example, a distributor of the injection device 10, a distributor of the packaging assembly 100, a healthcare professional or caregiver or an authorised third-party.

The dosing time period for a type of injection device 10 represents the period of time required between each scheduled dosing time for the device type. The dosing time period for each injection device 10 may be recorded on the device tag 30 and transmitted to the device sensor 241. Alternatively, a dosing time period for one or more types of injection device 10 may be stored in the non-volatile memory 233 of the electronics system 200. The processor arrangement 230 may record the dosing time period for an injection device 10 in the device table based on the device information received from the device sensor 241.

The processor arrangement 230 generates an active countdown timer for each type of injection device 10 stored in the packaging assembly 100. Each active countdown timer is a countdown operation performed by the processor arrangement 230 as described above. The countdown time for each device type is initiated with the number of days specified by the dosing time period.

The expiry date of an injection device 10 represents the latest date on which the injection device 10 is considered suitable for use. When the expiry date is in the past the injection device 10 is considered to be expired and should not be used. The processor arrangement 230 records an expired flag when the expiry date of an injection device 10 is in the past.

Alternatively, the processor arrangement 230 may compare the expiry date of an injection device 10 with the next scheduled dosing time for the injection device 10. The processor arrangement 230 may already record an expired flag when the expiry date of the injection device 10 will pass before the next scheduled dosing time becomes due. The processor arrangement 230 may be further configured to record an expired flag if the injection device 10 is not suitable for use for any other reason. For example, if the internal temperature of the packaging assembly 100 is recorded as being too high for a predefined period of time, the processor arrangement 230 may record an expired flag for one or more injection devices 10 stored therein.

The processor arrangement 230 may receive device information for each injection device 10 through the wireless communication module 260. Any of the device ID, device type, dosing time period and expiry date may be received by the processor arrangement 230 through the wireless communication module 260. The device information for each injection device 10 may be pre-stored in an external device 300 and transmitted to the wireless communication module 260. The processor arrangement 230 may transmit the device ID for an injection device 10 to an external device 300 with a request for additional device information for the injection device 10. Device information received through the wireless communication module 260 may replace or update device information previously stored by the processor arrangement 230. For example, the dosing time period for an injection device 10 may be updated remotely by an external device 300. The user of the external device 300 may be any of, for example, a distributor of the injection device 10, a distributor of the packaging assembly 100, a healthcare professional or caregiver or an authorised third-party.

The electronics system 200 comprises a reset switch 215. The reset switch 215 is configured to provide a signal to the processor arrangement 230 when actuated by the reset button 164. The user presses the reset button 164 to indicate that the scheduled dosage has taken place, and to reset the time period for the next scheduled dosing time.

The reset switch 215 may be a mechanical switch mounted on the PCB 201. The reset switch 215 is arranged to be actuated by the reset button 164. The reset switch 215 may be a normally open switch having an open state and a closed state. The reset switch 215 may be operated to move from the open state to the closed state when pressed. The reset switch 215 may be configured to pass a current in a closed state only. The reset switch 215 may be configured to provide a signal to the processor arrangement 230 when moved to the closed state.

The reset button 164 may be coupled to the reset switch 215. The reset switch 215 may be positioned below the reset button 164. If the reset button 164 is pressed, the reset switch 215 may be moved to the closed state by the reset button 164. The reset switch 215 is configured to provide a signal to the processor arrangement 230 when actuated by the reset button 164. The processor arrangement 230 is configured to reset a countdown operation in response to the signal from the reset switch 215.

The processor arrangement 230 is configured to operate a reset timer. The processor arrangement 230 is configured to reset the time period for the next scheduled dosing time when the time period measured by the reset timer is over 2 seconds. The reset timer is started from zero when the reset switch 215 is moved to the closed state. Alternatively, the reset timer may be started at 2 seconds when the reset switch 215 is closed and count down such that the timer expires if the reset switch is not opened within 2 seconds.

The user must press and hold the reset button 164 for 2 seconds to maintain the reset switch 215 in the closed state for 2 seconds. The processor arrangement 230 filters out short presses of the reset button 164, so as to reduce the occurrence of falsely triggering the reset operation.

The electronics system 200 comprises the display 211 of the user interface 210. The display 211 can be operated to provide a notification. The display 211 can be operated to provide an indication of a status of the packaging assembly 100. The display 211 is an example of a status indicator. The display 211 can be operated to show any number from 00 to 99 by illuminating some or all of the LED segments. Certain letters may also be shown by the display 211.

The electronics system 200 may comprise a display driver 235. The display driver 235 may be provided as a separate integrated circuit chip to the processor arrangement 230, which is connected by an off-chip bus. Alternatively, the display driver 235 may be provided on a single integrated circuit chip with the processor arrangement 230. The display driver 235 may be a port expander for individually controlling the segments of a seven-segment LED display.

The processor arrangement 230 can operate the display 211 to show the number of days remaining until the next scheduled dosing time is due. The processor arrangement 230 is configured to determine the lowest active countdown timer, that is, the countdown timer with the fewest days remaining. The display 211 can be operated to show the number of days remaining on the lowest active countdown timer. The display 211 can be operated to provide a visual reminder output that the scheduled dosing time is due. The display 211 can be operated further to provide a visual reminder output that the scheduled dosing time is near.

The display 211 can be operated to show information relating to the status of the packaging assembly 100. The processor arrangement 230 may check the state of charge of one or more batteries 170 included in the packaging assembly 100. If the state of charge is determined to be low, the display 211 may be operated to show a battery low warning.

The electronics system 200 comprises the LED array 220 of the user interface 210. The LED array 220 can be operated to provide a notification. LED array 220 can be operated to provide an indication of a status of the packaging assembly 100. The LED array 220 is an example of a status indicator.

The processor arrangement 230 can operate the LED array 220 to provide a visual reminder that a scheduled dosing time is due. On the day of a scheduled dosing time, the LED array 220 is operated to generate a visual reminder output. The processor arrangement 230 can operate the LED array 220 to provide a visual indication that an injection device 10 is expired. The processor arrangement 230 can operate the LED array 220 to provide a visual indication that an injection device 10 is not located in one of the openings 151. The processor arrangement 230 can operate the LED array 220 to provide a visual indication that the status of an injection device 10 is normal.

The LED array 220 comprises an array of eighteen light-emitting diodes (LEDs). The LEDs of the LED array 220 are arranged on the panel 150, in proximity to the openings 151. The LED array 220 comprises three LEDs 221,222,223 for each of the six openings 151. Each of the three LEDs 221,222,223 can be illuminated with a different colour. For example, the LED array 220 may comprise a blue LED 221, a white LED 222 and a red LED 223 for each opening 151.

The white LED 222 corresponding to an opening 151 may be operated to provide a visual indication that the opening 151 is empty. The red LED 223 corresponding to an opening 151 may be operated to provide a visual indication that the injection device 10 located in the opening 151 has expired.

The blue LED 221 corresponding to an opening 151 may be operated to flash or blink to provide a visual reminder that the scheduled dosing time is due for the injection device 10 stored in the opening 151. The flash periodicity of the blue LED 221 output may be of the order of 0.25 seconds to 2 seconds. The blue LED 221 may be further operated to illuminate continuously to provide a visual indication that the injection device 10 located in the opening 151 has a normal status.

The electronics system 200 comprises the speaker 213 of the user interface 210. The speaker 213 can be operated to output a notification signal. The speaker 213 can be operated to provide an indication of a status of the packaging assembly 100. The speaker 213 is an example of a status indicator.

The processor arrangement 230 operates the speaker 213 to provide an audio reminder that the next scheduled dosing time is due. On the day of a scheduled dosing time, the speaker 213 is operated to output an audio reminder that the schedule dosage time is due. The speaker 213 may be operated to output an intermittent tone or tone sequence. The periodicity of the intermittent speaker 213 output may be of the order of 0.25 seconds to 2 seconds. The processor arrangement 230 may control the operation of the speaker 213 according to the signal input by the lid open sensor 252. The audio reminder output by the speaker 213 may be deactivated when the lid is opened.

The processor arrangement 230 controls the user interface 210 according to an input from the fridge open sensor 251. If the fridge open sensor 251 indicates by signalling to the processor arrangement 230 that the fridge door is open, the processor arrangement 230 controls the user interface 210 as described above. If the fridge open sensor 251 does not indicate by signalling to the processor arrangement 230, the processor arrangement 230 does not activate the user interface 210.

In this way, the user interface 210 is not active when the fridge is closed. The user interface 210 of the packaging assembly 100 is activated only when the fridge is open, therefore conserving the energy of the battery 170. The processor arrangement 230 may further control the user interface 210 according to whether the wireless communication module 260 has established communication with a recognized external device 300. In the way, the user interface 210 can be prevented from activating when the fridge is opened by someone other than the patient.

The electronics system 200 comprises a wireless communication module 260. The wireless communication module 260 is configured to transmit and receive signals wirelessly, under the control of the processor arrangement 230. The wireless communication module 260 comprises one or more antennae for the transmission and reception of radio-frequency (RF) signals. The wireless communication module 260 may be configured to communicate using one or more wireless protocols such as Bluetooth, Zigbee, Wi-Fi or similar. Alternatively, or in addition, the wireless communication module 260 may comprise an optical transmitter and receiver for communication using an optical protocol such as Li-Fi, Infra-red Data Association (IrDA) or similar.

The processor arrangement 230 controls the wireless communication module 260 according to an input from the fridge open sensor 251. If the fridge open sensor 251 indicates by signalling to the processor arrangement 230 that the fridge door is open, the processor arrangement 230 controls the wireless communication module 260 to establish communication with an external device 300. If the fridge open sensor 251 does not indicate by signalling to the processor arrangement 230, the processor arrangement 230 does not activate the wireless communication module 260. The wireless communication module 260 is activated only when the fridge is open, therefore conserving the energy of the battery 170.

The processor arrangement 230 is configured to start the door timer from zero when the fridge door is opened. After the timer has been started, the device can be said to be in a door open state. The processor arrangement 230 is configured to enter a partial sleep state when the time period measured by the door timer is over 5 minutes. The user interface 210 is turned off by the processor arrangement 230 in the partial sleep state, and the processor arrangement operates at the stand-by clock speed. The processor arrangement 230 operates the wireless communication module 260 to transmit an alert message when the time period measured by the door timer is over 5 minutes.

The electronics system 200 comprises a locking mechanism 270. The locking mechanism 270 is configured to lock the position of the lid 120 when activated. The locking mechanism may be a solenoid actuator positioned to engage with a corresponding hole in the lid 120.

Figure 6:
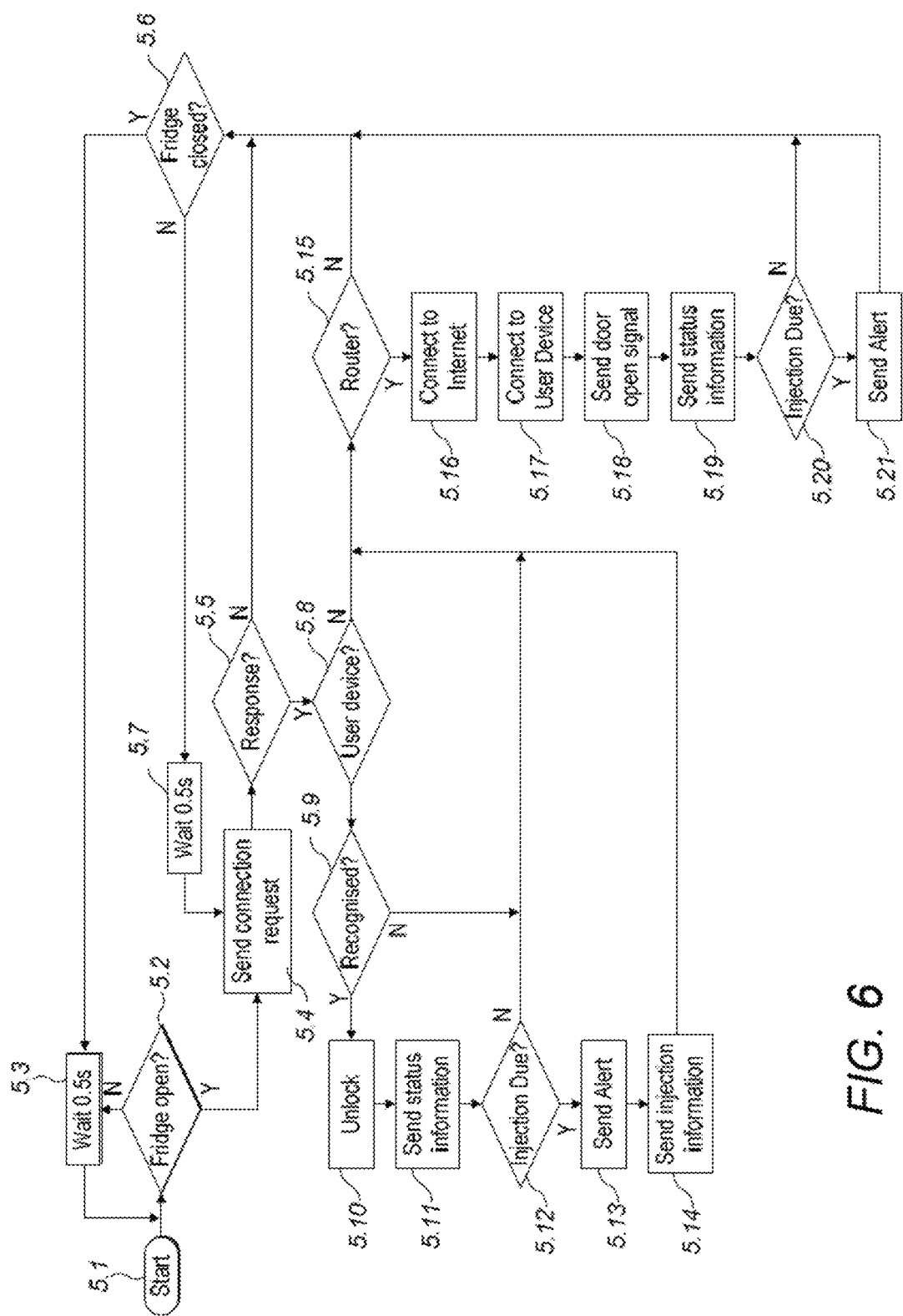
FIG. 6 is a flowchart illustrating a second exemplary operation of the packaging assembly, according to an exemplary embodiment.

With respect to FIG. 6, a flowchart showing a wireless communication operation of the electronics system 200 is shown.

The process starts at step 5.1.

At step 5.2, the processor arrangement 230 checks whether or not the fridge door is open. The processor arrangement 230 checks whether a signal to indicate that fridge door is open is received from the fridge open sensor 251. If a signal is not received, the processor arrangement 230 proceeds to step 5.3. At step 5.3 the processor arrangement 230 waits 0.5 seconds before returning to step 5.2 and checking again whether or not the fridge is open. If a signal indicating that the fridge door is open is received by the processor arrangement 230, the processor arrangement 230 proceeds to step 5.4.

At step 5.4, the wireless communication module 260 sends a connection request. The wireless communication module 260 is activated by the processor arrangement 230 and is operated to broadcast a wireless signal. The wireless communication module 260 broadcasts a request for communication using at least one wireless protocol. For example, the wireless communication module 260 broadcasts a Bluetooth discovery announcement.

At step 5.5, the wireless communication module 260 monitors the receive channel for a response from an external device 300. If the wireless communication module 260 does not indicate to the processor arrangement 230 that a response has been received, the processor arrangement 230 proceeds to step 5.6. At step 5.6, the processor arrangement 230 checks whether the fridge door has been closed. The processor arrangement 230 checks whether a signal to indicate that fridge door is open is still received from the fridge open sensor 251.

If the fridge door has been closed, the processor arrangement 230 returns to step 5.3, waiting 0.5 seconds before continuing to monitor the fridge door. While the fridge door remains open, the processor arrangement 230 proceeds to step 5.7 and waits 0.5 seconds, before returning to step 5.4 and operating the wireless communication module 260 to send a further connection request.

When the wireless communication module 260 receives a response signal, the wireless communication module 260 provides the received signal to the processor arrangement 230, and the processor arrangement 230 proceeds to step 5.8. At step 5.8, the processor arrangement 230 determines whether the detected external device 300 is a first external device 300a, that is, a user device. The processor arrangement 230 determines whether the external device is, for example, a mobile phone or personal internet device. The external device 300 may be identified as the first external device 300a in the response signal received by the wireless communication module 260. If the external device 300 is not already identified, the processor arrangement 230 may operate the wireless communication module 260 to request the identity of the external device 300.

If the external device 300 provides a response which identifies the device to be the first external device 300a, the processor arrangement 230 proceeds to step 5.9. If the external device 300 cannot be identified as the first external device 300a, the processor arrangement 230 proceeds to step 5.15.

At step 5.9, the processor arrangement 230 is checks whether the first external device 300a is a recognised device. The processor arrangement 230 compares a received identifier of the first external device 300a, such as a physical layer address of the device, with a list of one or more recognised user devices in the non-volatile memory 233. Alternatively, the processor arrangement 230 may operate the wireless communication module 260 to transmit a request for user authentication to the first external device 300a. The wireless communication module 260 may transmit a request for a PIN or password or similar to be input by the user of the first external device 300a.

If the first external device 300a cannot be recognised, the processor arrangement 230 operates the wireless communication module 260 to terminate communication with the first external device 300a and proceeds to step 5.15. No status or device information is transmitted to the user device 300a. In addition, the lid 120 of the packaging assembly 100 may remain locked, and the user interface 210 may remain inactive.

If the user device 300a is recognised by the processor arrangement 230, the processor arrangement 230 proceeds to step 5.10. At step 5.10, the processor arrangement 230 operates a locking mechanism 270 of the lid 120 to unlock and allow the lid 120 to be opened by the user. At step 5.11, the processor arrangement 230 operates the wireless communication module 260 to transmit status information of the packaging assembly to the first external device 300a.

The processor arrangement 230 determines the internal temperature and humidity of the packaging assembly 100 from the temperature sensor 253 and the humidity sensor 254 respectively. The wireless communication module 260 may transmit the determined temperature and humidity values or may transmit a signal to indicate whether or not each of the temperature and humidity is over a threshold. The wireless communication module 260 may further transmit status information for one or more injection devices 10 stored in the packaging assembly 100. The wireless communication module 260 may transmit device information, for example, the number and types of injection devices 10 stored in the packaging assembly 100.

The wireless communication module 260 may transmit a signal to the first external device 300a if one or more of the injection devices 10 has expired.

At step 5.12, the processor arrangement 230 checks whether a scheduled dosing time is due for one or more injection devices 10 stored in the packaging assembly 100. The processor arrangement 230 checks whether one or more countdown timers have reached zero. If the countdown to a schedule dosing time is zero days, then the processor arrangement 230 determines that the scheduled dosing time is due, and proceeds to step 5.13. Otherwise, if a scheduled dosing time is not due, the processor arrangement 230 proceeds to step 5.15.

At step 5.13, the processor arrangement 230 operates the wireless communication module 260 to transmit a signal to the first external device 300a to indicate that the scheduled dosing time is due.

At step 5.14, the processor arrangement 230 operates the wireless communication module 260 to transmit injection information to the first external device 300a. The wireless communication module 260 may transmit a warm-up time period to the first external device 300a, representing the recommended period of time to wait before injection to allow the injection device 10 to reach room temperature. The warm-up time period for an injection device 10 may be stored in the non-volatile memory 233 or may be received by the device sensor 241 from the injection device 10.

The wireless communication module 260 may further transmit instructions for the use of the injection device 10 to the first external device 300a. Instructions may be transmitted in the form of text, diagrams or audio or video instructions. Instructions for the use of the injection device 10 may be stored in the non-volatile memory 233 or may be received by the device sensor 241 from the injection device 10.

If the external device 300 cannot be identified as the first external device 300a or cannot be recognised, the processor arrangement 230 proceeds to step 5.15. At step 5.15, the processor arrangement 230 determines whether the detected external device 300 is the wireless terminal 300c. The processor arrangement determines if the external device 300 is, for example, a router device configured as a wireless access point.

The processor arrangement 230 may recognise the external device 300 as the wireless terminal 300c, based on a previous connection to the external device 300. The processor arrangement 230 may determine that the external device 300 is configured as a wireless access point based on a service discovery signal transmitted by the external device 300. If the external device 300 is determined to be the wireless terminal 300c, the processor arrangement 230 proceeds to step 5.16. Otherwise, if the external device 300 is not the wireless terminal 300c, the processor arrangement 230 returns to step 5.6.

At step 5.16, the processor arrangement 230 operates the wireless communication module 260 to join a wireless LAN set up by the wireless terminal 300c and connects to the internet through the wireless terminal 300c. The processor arrangement 230 may require authentication to join the wireless LAN and/or to connect to the internet. Authentication information may be stored in the non-volatile memory 233. Authentication information may be input by a user or may be received from a connected first external device 300a by the wireless communication module 260.

At step 5.17, the processor arrangement 230 operates the wireless communication module 260 to connect to the second external device 300b through the internet. Network address information for the second external device 300b may be stored in the non-volatile memory 233. For example, the non-volatile memory 233 may store an IP address, a URI or URL of the second external device 300b.

At step 5.18, the processor arrangement 230 operates the wireless communication module 260 to transmit a signal to the second external device 300b to indicate that the fridge door is open. The wireless communication module 260 may transmit a further signal to the second external device 300b to indicate whether the lid 120 is opened and closed. The wireless communication module 260 may transmit a further signal if the sensor array 240 detects the removal of an injection device 10 from the packaging assembly 100. In this way, the packaging assembly 100 allows a caregiver to remotely monitor the patient's compliance with the dosing schedule.

At step 5.19, the processor arrangement 230 operates the wireless communication module 260 to transmit status information of the packaging assembly 100 to the second externa device 300b. The processor arrangement 230 determines the internal temperature and humidity of the packaging assembly from the temperature sensor 253 and the humidity sensor 254 respectively. The wireless communication module 260 may transmit the determined temperature and humidity values or may transmit a signal to indicate whether or not each of the temperature and humidity is over a threshold. The wireless communication module 260 may further transmit status information for one or more injection devices 10 stored in the packaging assembly 100. The wireless communication module 260 may transmit device information, for example, the number and types of injection devices 10 stored in the packaging assembly 100. The wireless communication module 260 may transmit a signal to the second external device 300b if one or more of the injection devices 10 has expired.

At step 5.20, the processor arrangement 230 checks whether a scheduled dosing time is due for one or more injection devices 10 stored in the packaging assembly 100. The processor arrangement 230 checks whether one or more countdown timers have reached zero. If the countdown to a schedule dosing time is zero days, then the processor arrangement 230 determines that the scheduled dosing time is due, and proceeds to step 5.21. At step 5.21, the processor arrangement 230 operates the wireless communication module 260 to transmit a signal to the second external device 300b to indicate that the scheduled dosing time is due. Otherwise, if a scheduled dosing time is not due, the processor arrangement 230 returns to step 5.6.

Figure 7A:
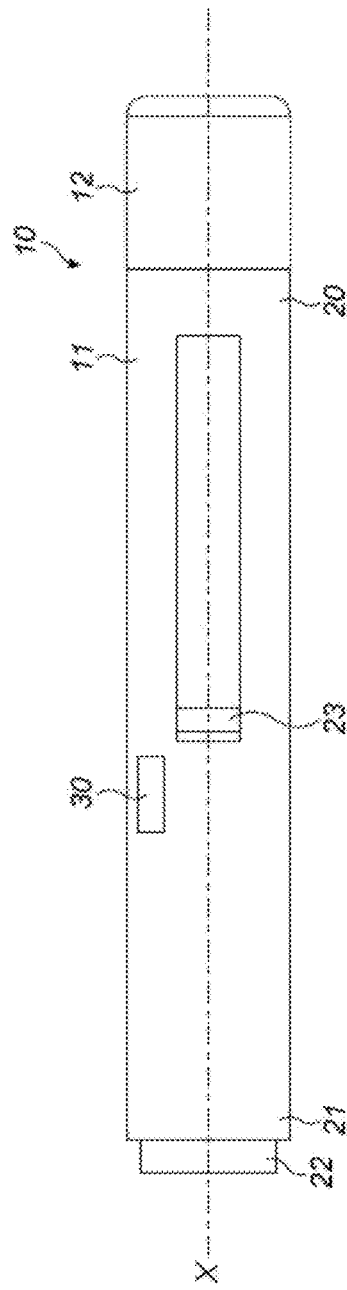
FIGS. 7A and 7B are side-on views of an auto-injection device for use with the packaging assembly, according to an exemplary embodiment.
Figure 7B:
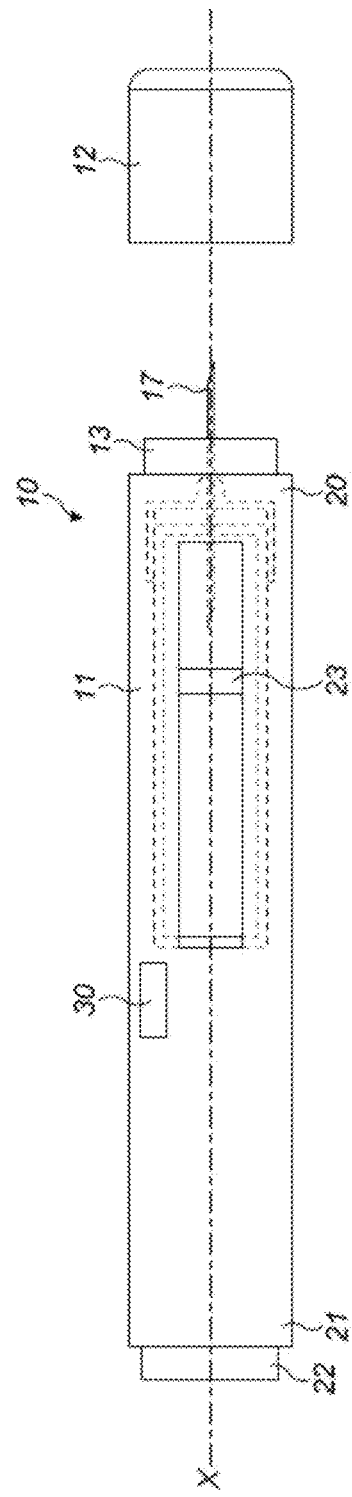

With respect to FIGS. 7A and 7B, an exemplary injection device 10 is shown. Injection device 10, as described above, is configured to inject a medicament into a user's body. Injection device 10 includes a housing 11 which typically contains a reservoir containing the medicament to be injected (e.g., a syringe) and the components required to facilitate one or more steps of the delivery process. Injection device 10 can also include a cap assembly 12 that can be detachably mounted to the housing 11. Typically a user must remove cap 12 from housing 11 before injection device 10 can be operated.

As shown, housing 11 is substantially cylindrical and has a substantially constant diameter along the longitudinal axis X. The housing 11 has a proximal region 20 and a distal region 21. The term "proximal" refers to a location that is relatively closer to a site of injection, and the term "distal" refers to a location that is relatively further away from the injection site.

Injection device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a distal direction can permit a needle 17 to extend from proximal region 20 of housing 11.

Insertion of needle 17 can occur via several mechanisms. For example, needle 17 may be fixedly located relative to housing 11 and initially be located within an extended needle sleeve 13. Distal movement of sleeve 13 by placing a proximal end of sleeve 13 against a user's body and moving housing 11 in a proximal direction will uncover the distal end of needle 17. Such relative movement allows the proximal end of needle 17 to extend into the user's body. Such insertion is termed "manual" insertion as needle 17 is manually inserted via the user's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 6A & 6B, button 22 is located at a distal end of housing 11. However, in other embodiments, button 22 could be located on a side of housing 11.

Other manual or automated features can include drug injection or needle retraction, or both. Injection is the process by which a bung or piston 23 is moved from a distal location within a syringe to a more proximal location within the syringe to force a medicament from the syringe through needle 17. In some embodiments, a drive spring is under compression before device 10 is activated. A distal end of the drive spring can be fixed within distal region 21 of housing 11, and a proximal end of the drive spring can be configured to apply a compressive force to a distal surface of piston 23. Following activation, at least part of the energy stored in the drive spring can be applied to the distal surface of piston 23. This compressive force can act on piston 23 to move it in a proximal direction. Such proximal movement acts to compress the liquid medicament within the syringe, forcing it out of needle 17.

Following injection, needle 17 can be retracted within sleeve 13 or housing 11. Retraction can occur when sleeve 13 moves proximally as a user removes device 10 from a user's body. This can occur as needle 17 remains fixedly located relative to housing 11. Once a proximal end of sleeve 13 has moved past a proximal end of needle 17, and needle 17 is covered, sleeve 13 can be locked. Such locking can include locking any distal movement of sleeve 13 relative to housing 11.

Another form of needle retraction can occur if needle 17 is moved relative to housing 11. Such movement can occur if the syringe within housing 11 is moved in a distal direction relative to housing 11. This distal movement can be achieved by using a retraction spring located in proximal region 20. A compressed retraction spring, when activated, can supply sufficient force to the syringe to move it in a distal direction. Following sufficient retraction, any relative movement between needle 17 and housing 11 can be locked with a locking mechanism. In addition, button 22 or other components of device 10 can be locked as required.

Injection device 10 comprises a device tag 30, for example, a passive RFID tag. The device tag 30 may internally or externally mounted on the housing 11. The device tag 30 is configured to activate when placed in an electromagnetic field, and to output a response signal when activated.

The device tag 30 is arranged at a midpoint of the housing 11, between proximal region 20 and distal region 21. The device tag 30 is arranged to align with the device sensor 241 when the injection device 10 is moved through the opening 151 of the packaging assembly 100. In this way, the device tags 30 of injection devices 10 stored in the packaging assembly 100 are separated from the sensor array 240, improving the clarity of detection. Furthermore, the speed of the injection device 10 is generally greatest as the midpoint of the injection device 10 is moving through the opening 151. The device tag 30 is therefore activated for a shorter period of time, and the power consumption of the device sensor 241 can be minimised.

The response signal of the device tag 30 may include information related to the injection device 10. Information may be stored on the device tag 30 and transmitted as part of the response signal when the device tag 30 is activated. The device tag 30 may store one or more of a device ID, device type, expiry date, dosing time period and warm-up time period of the injection device 10.

The packaging assembly 100 may contain or store a plurality of different types of injection device 10 with different information stored on each device tag 30. Each injection device 10 may have a different expiry date, dosing time period and/or warm-up time period stored in the device tag 30.

It will be appreciated that the above described embodiments are purely illustrative and are not limiting on the scope of the claims. Other variations and modifications will be apparent to persons skilled in the art upon reading the present application, and some will now be described.

The case of the packaging arrangement may be a generally rectangular shape or may be any other shape suitable for containing the plurality of injection devices. The case may be a suitable shape and size for placement within a household refrigerator.

The case may be formed to enclose the injection devices and may be sealed, Alternatively, the case may be formed as a structure for supporting the plurality of injection devices externally. The injection devices may be arranged in one or more rows, e.g. a row of six or two rows of three, or in a circular arrangement. The injection devices may be arranged to hang below a supporting structure.

The case may be configured to store any number of injection devices, according to the dosage requirements of the medicament. For example, the case may store between 5 and 15 injection devices. Case may be sized to store enough injection devices for one quarter, or for a 6 month period. Where medicament is administered more regularly, the case may store enough injection devices for one week.

The case may be formed of an opaque material. One or more of the components of the case may be formed with at least a transparent portion. A transparent portion of the case may allow the user to see the number of injection devices, or to see the user interface. One or more components of the case may be translucent to improve visibility of a visual reminder output.

The case may be formed of a plastics material such as polyethylene, polystyrene, polycarbonate, or it may be made of any other suitable material. Desired properties for the material of the case include temperature stability, moderate impact strength, resistance to cleaning fluids, a wipe-clean finish, and rigidity.

Each part of the case may be formed in a single piece e.g. a moulded plastic part. Alternatively, parts may be machined. The body of the case may be formed from two parts joined or attached together, or may be formed in a single part. An internal of the case may be formed as a single large cavity, a cavity divided into a plurality of areas for holding each injection device, or may be formed as a plurality of cavities for individually holding each injection device.

The case may comprise any number of magnets sufficient to support the weight of the packaging arrangement and injection devices. For example, the case may include 2 larger magnets or an arrangement of 6 smaller magnets. The magnets may be any permanent magnets and may be rare earth magnets. The magnets may be formed of neodymium or may be formed of samarium cobalt.

The case may further comprise one or more ventilating apertures to allow air flow into the case. Alternatively, the case may be sealed when the lid is in a closed position. The lid may further comprise a rubber seal to prevent air passing into the case between the lid and the case. The case may be insulated to maintain the low temperature of the injection devices if removed from the fridge for a short period of time.

The lid may be coupled to the case with a hinge. The mechanism for connecting the lid to the case and for allowing the lid to open and close may take any suitable form. Instead of the hinge mechanism described above, the hinge may be a butt hinge, a living hinge or some other type.

The lid may be coupled to the case with a flexible and/or elastic material. The hinge may allow some translational movement as well as pure rotational movement, to allow better viewing of or access to the internal part of the case when the lid is open.

The hinge may allow the removal of the lid by a user. For instance, the protrusions of each of the second hinging parts may be pushed inwards to disengage from the respective first hinging parts and decouple the lid from the case. The user may be provided with one or more alternative lids which may be a different design, for example, a different colour. An alternative lid may have a larger transparent portion or may be entirely opaque.

Alternatively, the lid may slidably engage with the case. The lid may comprise runners at the edges, each configured to engage with a corresponding groove on the case. The lid may slide out of the grooves and decouple from the case. The lid may be arranged to slide to the limit of the grooves and pivot freely in the open position. Further alternatively, the lid may be separate from the case and fixedly attached thereto with a friction fit. The lid may fit tightly within the opening at the upper end of the case, or may fit over an upper portion of the case.

The lid may comprise a latch to maintain the lid in the closed position. The latch may comprise a sliding catch arranged to slidably move between a first position and a second position. The catch may be arranged to protrude from an edge of the lid in the first position. The catch may be configured to slidably retract to not protrude in the second position. The latch may comprise a spring to urge the catch to the first position. The catch may be configured to engage with an opening in the case in the first position when the lid is in the closed position. The catch may engage with the opening to maintain the lid in the closed position.

The latch may be a sprung push-catch push-release mechanism. The latch may be configured to engage with a first push into the closed position and maintain the lid in the closed position. The latch may be configured to disengage with a second push and allow the lid to open. The latch may be configured to engage when the lid is closed to hold the lid in the closed position. The latch may further comprise a release switch to disengage the latch and allow the lid to open. The release switch may be a mechanical switch or an electric switch. The release switch may be an electric switch coupled to a code input, which is configured to disengage the lid catch when a correct code is entered.

Although the lid open sensor is described as an electromechanical switch, it may instead be an optical sensor arrangement, a magnetic sensor arrangement or any other suitable arrangement that is configured to detect whether the lid is open or closed or whether the lid is transitioning from a closed position to an open position.

The packaging assembly may comprise a case without a lid. The packaging assembly may not include a lid open sensor. The speaker may instead be deactivated by the processor arrangement according to an alert timer. The processor arrangement may be configured to operate the alert timer. The processor arrangement may activate the alert timer when the speaker is controlled to output an audio reminder alert that the scheduled dosing time is due. The processor arrangement may activate the alert timer when the scheduled dosing time is due, conditional on the fridge door being open. The processor arrangement may deactivate the speaker when the alert timer reaches 30 seconds. Alternatively, the processor arrangement may activate the alert timer at 20 seconds and count down until the timer expires. The processor arrangement may be configured to deactivate the speaker when the alert timer expires. The expiry time period for the alert timer may be 5 seconds to 60 seconds.

The electronics system may include a device sensor to determine whether an injection device is positioned in one of the plurality of openings. The device sensor may determine whether an injection device is positioned within each of the openings. The processor arrangement may be configured to deactivate the speaker when the device sensor indicates that an injection device has been removed from an opening.

The device sensor may comprise one or more device switches. The device switches may be arranged respectively within the openings. Each device switch may be a mechanical switch. The device switch may be a normally open switch which is pressed to a closed position by an injection device when in position in the opening. The device switch may be a membrane switch. The device switch may be actuated by a lever located within the opening.

Each device switch may be configured to send a signal to the processor arrangement when an injection device is located within the corresponding opening. The processor arrangement may be configured to activate or deactivate the speaker when a signal is no longer received from a device switch. The processor arrangement may be configured further to reset the countdown to the scheduled dosing time when an injection device is removed from the opening. Alternatively, where an injection device is replaced in the case after the dose is administered, the processor arrangement may be configured to reset the countdown when the injection device is replaced. The processor arrangement may be configured to monitor the number of injection devices in position in the packaging assembly. The processor arrangement may control the display to show the number of injection devices in the packaging assembly. The processor arrangement may control the electronics system to provide a notification output when the packaging assembly is empty.

The retention mechanism may be arranged at the lower end of the case. The retention mechanism may be arranged to engage with the end of each injection device which is passed through the opening. The retention mechanism may comprise a further plurality of openings at the lower end of the case. The further openings may be sized so as to hold the injection devices in position with a friction fit. Alternatively, the retention mechanism may comprise a levered pincer arrangement arranged to grip the sides of an injection device when the injection device is pushed longitudinally into the arrangement, and to release the injection device when the injection device is pulled longitudinally out of the arrangement.

The retention mechanism may comprise a release switch configured to disengage the retention mechanism. The release switch may be configured to release one or all of the injection devices. A plurality of release switches may be provided for the corresponding plurality of injection devices. The release switch may be a mechanical switch or lever coupled to the retention mechanism. The release switch may be further coupled to an ejection mechanism. The release switch may be an electromechanical switch. The release switch may be controlled by the processor arrangement. The processor arrangement may control the release switch to disengage the retention mechanism conditional on the scheduled dosing time being due. The processor arrangement may control the release switch to disengage the retention mechanism for one injection device when the scheduled dosing time is due.

The ejection mechanism may comprise one or more springs arranged to push a portion of the respective injection devices out of the corresponding openings. The ejection mechanism may be biased against the retention mechanism to push each injection device when released by the retention mechanism. The retention mechanism may be controlled to release one injection device, which is pushed partially out of the opening by the ejection mechanism. This arrangement may provide a visual reminder alert in the form of a portion of the injection device being pushed out of the opening.

Alternatively, the ejection mechanism may comprise a motorised actuator. For example, a roller arranged perpendicularly to the plurality of injection devices may be driven to push the injection devices out of the openings. The roller may push all of the injection devices equally, with the retention mechanism configured to hold all but one of the injection devices in position. Further alternatively, the actuator may comprise a protruding part from the base of the case which is driven laterally across the width of the case. The protruding part may be driven along a rail, or may protrude from a belt extending along the width of the case. The protruding part is configured to engage with each injection device in turn and push the injection device out of the opening.

The time period for a reminder may be any suitable dosing period, dependent upon the medicament which is stored in the packaging assembly. The time period set until the next scheduled dosing time may be any number of days and may be, for example, between 2 and 60 days. The time period may be a number of weeks, for example, a period of 7 days, 14 days, 21 days or 28 days. The time period may be 28 days, which is 4 weeks, or the time period may be 1 month. A different time period may be set for each injection device. The time period for an injection device may be recorded on the injection device and may be read by the device sensor. The time period for a type of injection device may be stored in the non-volatile memory.

The time period may be 1 or 2 days, and the display may be configured to show the number of hours until the scheduled dosing time is due. Similarly, for a time period on the order of a number of hours, the display may show a number of minutes.

A time period may be fixed for all injection devices. A predetermined time period may be stored in the non-volatile memory. Alternatively, a timer duration switch may be configured to select between any two time periods. For example, a first switch position may correspond to a time period of 7 days and a second switch position may correspond to a time period of 14 days. Alternatively, the timer duration switch may be a multi-positional switch, for example, a rotary switch or a dial. The time period may be set in conjunction with the display, wherein a first user input causes the display to show the current time period, and a second input is used to adjust the time period.

Alternatively, the time period may be adjusted with a specific sequence of inputs using the reset button. For example, holding the reset button for a longer period of time, e.g. longer than 5 seconds, may initiate a "time period adjustment mode". The display may show the current timer duration, e.g. the display may show "14" to indicate 14 days. In this mode, pushing the reset button again for less than 5 seconds may increase the period incrementally. For example, a single button push may add 1 day, and the displayed value is changed accordingly. In this way, the user can adjust the period up to a predefined maximum value, e.g. "28". If the user pushes another time, then the time period may be dropped to a predefined minimum value, e.g. "14".

If the user again holds the reset button for a longer period of time, e.g. longer than 5 seconds, the currently displayed value may be stored as the new time period and the normal operation is resumed. Alternatively, the value may be stored and normal operation resumed after a predetermined period with no input, e.g. after 10 seconds.

The door timer and reset timer may operate on any suitable timeframe. For example, the user interface 210 may enter the partial sleep mode if the fridge door is open for 10 minutes or 15 minutes. The reset button may be configured to reset the countdown timer if pressed for 1 second or up to 5 seconds.

The display may comprise more than 2 LED arrays, to accommodate larger numbers and messages, or more be a single LED array only. Alternatively, the display may comprise any form of electronic display suitable for displaying a number and/or a message, for example, the display may be an array of LED pixels, an LCD or e-paper screen, or a split-flap display. The display may be a display which is capable of displaying pseudo-3D images or video, e.g. a lenticular display. The display may be arranged in a peripheral module which is separate from the case. The display module may be connected to the electronics system with a wired or wireless connection. The electronics system may comprise any display driver which is suitable for chosen display.

The display may be configured to provide further status information, or more detail, in the form of text messages on the display. For example, the display may provide a visual reminder that the scheduled dosing time is due by showing a reminder message in addition to, or instead of, flashing the number 00. The output of the number 00 is an example of a reminder message. The display may be controlled to show the number of injection devices remaining in the packaging assembly. The processor arrangement may be configured to determine the number of injection devices according to an input from the sensor array. Alternatively, the processor arrangement may be configured to monitor the number of times that a scheduled dosing time has passed. The display may be controlled to show a notification message when the packaging assembly is empty.

The display may be used to display a short sequence of pictures or a video, in 2D or in 3D, to show the correct usage or application of the injection device. The display may show any other useful information or advice connected to the therapy or the daily life of the patient.

The display may be controlled to display a warm-up time period when an injection device is removed from the packaging assembly. The display may be controlled in conjunction with the sensor array. When the scheduled dosing time for an injection device is due, the sensor array may be operated to detect the removal of the injection device. The display may display the warm-up time period when the sensor array detects the removal of the injection device. The warm-up time period represents the recommend time required for the injection device to reach room temperature. The processor arrangement may perform a timing operation based on the warm-up time period.

The processor arrangement may be configured to deactivate the display of the user interface if the lid of the case is closed. The processor arrangement may activate the LED array based on the fridge open sensor, to indicate to the user that the status of the packaging assembly is normal, when the number of days remaining is greater than one, whether the lid is closed or not. The user may open the lid to activate the display and show the number of days if required. When the scheduled dosing time is due, the processor arrangement may activate both the LED array and the display to flash, to provide a visual reminder, whether the lid is open or not.

The processor arrangement may activate the LED array to indicate that the locking mechanism is active and the lid of the case is locked. For example, one or more red LEDs may be activated to indicate that the lid is locked. The one or more LEDs may be controlled to flash. The one or more activated LEDs will be visible through the translucent lid of the case. The processor arrangement may activate the LED array based on the fridge open sensor, to indicate that the case is locked when the fridge door is opened. The electronics system may further comprise one or more sensors to detect movement of the case or an attempt to open the lid of the case. The processor arrangement may activate the LED array based on a movement of the case or an attempt to open the lid of the case when the locking mechanism is active.

The LED array may include a plurality of LEDs for each of the plurality of openings or one LED per opening. For example, the LED array may include four, five or six LEDs per opening, to provide a greater variety of status information. Alternatively, two or three of the LEDs for each opening may be replaced by a single two-colour or three-colour LED. Alternatively, any other form of notification light or visual output transducer may be used in place of the LED. Alternatively, the processor arrangement may flash or blink one of the plurality of LEDs, while the remaining LEDs are off or illuminated continuously. A different LED may be controlled to blink each time, to guide the user to the next injection device for use. One LED may be flashed in a different colour. The processor arrangement may control a number of LEDs according to the number of injection devices remaining in the packaging assembly.

The speaker may be any suitable form of audio output transducer, for example, an electro-acoustic transducer, a piezoelectric buzzer, a moving diaphragm speaker, or a mechanical bell. A vibrating alert may be used instead of or in addition to the audio output transducer. The speaker may output a different alert output, according to the type of device. For example, the speaker may vary the periodicity of an intermittent tone, or the frequency of the tone, or may output a pre-defined tone sequence e.g. a 3-tone sequence. Alternatively, the speaker may be configured to reproduce a digital audio file stored in the non-volatile memory. A unique or individual alert may be used for each device type or, for example, to distinguish between alerts for different users of the packaging assembly. Audio alerts may be customisable by the user. In addition to an audio alert, the audio output of the speaker may be used to improve usability in other ways. For example, an audio output may indicate when an injection device is detected by the sensor array. A different audio output may be used according to whether the injection device is being inserted or removed.

An audio output may further provide an alarm function. The electronics system may further comprise one or more sensors to detect movement of the case or an attempt to open the lid of the case. The processor arrangement may activate the speaker based on a movement of the case or an attempt to open the lid of the case when the locking mechanism is active.

The fridge open sensor may comprise a phototransistor or, alternatively, a photoresistor or photodiode. Alternatively, the fridge open sensor may comprise a mechanical switch. The fridge open sensor may be located externally from the case and may be positioned at a hinge or frame of the fridge door. The fridge open sensor may be a mechanical switch which is arranged to be pressed by the fridge door in a closed position.

A wireless terminal may be located in close proximity to the fridge, located within the fridge or may be part of the fridge itself. The processor arrangement may activate the wireless communication module when the fridge door is closed to detect a wireless LAN of a nearby wireless terminal. The wireless communication module may be activated in this way on an occasional basis, for example, once per week or once every month or less. If a wireless LAN of a nearby wireless terminal is detected in this way, the processor arrangement may activate the wireless communication module to connect to the detected wireless LAN with increased regularity e.g. once per day or more.

The sensor array may be mounted on the panel, on a single PCB with the components of the electronics system. Alternatively, the sensor array may be mounted on a separate PCB. The sensor array may be positioned at the rear of the case, or internally on the upper or lower wall. A plurality of device sensors may be provided for each of the injection devices. The sensor array may alternatively comprise only a single device sensor. A single device sensor may activate and detect a plurality of device tags. The device sensor may determine the location of each device tag. Alternatively, a single device sensor may be externally positioned on the case, and the user may present each injection device to the device sensor before placing the injection device into the case.

Alternative device sensors may include optical sensors. Optical device tags such as, for example, barcodes or QR codes, may be provided on the plurality of injection devices. Alternatively, optical sensors may determine a colour or visual marking on an injection device to determine the type of injection device. In some embodiments, an optical sensor detects the presence of an injection device without receiving further device information. A device sensor may be implemented with a mechanical switch arranged to be pressed by an injection device when placed in the opening. The processor arrangement may determine the number of injection devices, the location of the injection devices and generate a device index for each injection device based on the detected presence of the injection devices. An alternative processor arrangement may iterate the device index only if both the device type and expiry date of an injection device match those of another injection device.

Alternative countdown timer implementations include off-chip and on-chip state-based logic circuits with clock devices, and other forms will be apparent to the skilled person.

The PCB and components of the electronics system may be sealed for protection. For example, the PCB may be coated on each side with a water resistant lacquer or another suitable coating. The electronics system may be coated for protection from moisture or humidity in the interior of a household fridge.

The packaging assembly may include a greater or smaller number of batteries, according to the power requirements of the electronics system. For example, the packaging assembly may include a single battery power pack. The battery or batteries may be removable and replaceable, or may be fixed within the case of the packaging assembly. Alternatively, the packaging assembly may be adapted for a mains power supply, or any alternative power supply.

The term "device type" is used to describe the physical sum of a drug container with a given drug and a given drug concentration, and the mechanical/electronical object performing relevant steps of the drug injection into the patient. The device type may be represented by one field in the device table or alternatively, for example, by two or more dependent fields to define the device type e.g. by specifying any of the medicament, concentration and delivery method of the injection device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary). The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about -4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoylgamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyhepta-decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F (ab) and F (ab') 2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F (ab') 2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the DR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A packaging assembly comprising:
    a case configured to at least partially contain a plurality of injection devices for delivering a medicament;
    a processor arrangement;
    a light sensor configured to detect light incident on the packaging assembly and to provide a signal to the processor arrangement according to the detected light intensity;
    a wireless communication module configured to establish a wireless connection with at least one external device conditional on an intensity of light detected by the light sensor exceeding a threshold light intensity; and
    a door open timer configured to be started in response to detecting that the intensity of light detected by the light sensor exceeds the threshold amount of light, and to expire after a predetermined time,
    wherein the wireless communication module is configured to transmit a door open alert to the at least one external device on expiry of the door open timer.

2. The packaging assembly of claim 1, wherein the processor arrangement is configured to enter a partial sleep state on expiry of the door open timer.

3. The packaging assembly of claim 1, wherein the predetermined time in in the range of 1 minute to 10 minutes.

4. The packaging assembly of claim 1, wherein the packaging assembly is configured to be stored in a fridge and the processor arrangement is configured, upon determining that the intensity of light detected by the light sensor exceeds the threshold amount of light, to determine that a door of the fridge is open.

5. The packaging assembly of claim 4, further comprising:
a temperature sensor configured to provide a signal to the processor arrangement according to the internal temperature of the packaging assembly,
wherein the processor arrangement is configured to compare the received signal to a threshold temperature, and
wherein the wireless communication module is configured to transmit an alert signal when the internal temperature of the packaging assembly exceeds the threshold temperature and conditional on the processor arrangement determining that the fridge door is open.

6. The packaging assembly of claim 5, wherein the threshold temperature is one of a preset threshold stored in a memory of the packaging assembly, or is dynamically adjustable having regard to operating conditions of the packaging assembly.

7. The packaging assembly of claim 4, further comprising:
a humidity sensor configured to provide a signal to the processor arrangement according to the internal humidity of the packaging assembly,
wherein the processor arrangement is configured to compare the received signal to a threshold humidity, and
wherein the wireless communication module is configured to transmit an alert signal when the internal humidity of the packaging assembly exceeds the threshold humidity and conditional on the processor arrangement determining that the fridge door is open.

8. The packaging assembly of claim 4, further configured to output a visual and/or audio reminder when a scheduled dosing time is due, wherein the visual and/or audio reminder is output conditional on the processor arrangement determining that the fridge door is open.

9. The packaging assembly of claim 8, wherein the packaging assembly further comprises:
a lid coupled to the case and movable between an open position and a closed position; and
a lid sensor configured to determine whether the lid is in the open position or the closed position,
and wherein the packaging assembly is configured to deactivate the visual and/or audio reminder upon detection of the lid being moved to the open position.

10. The packaging assembly of claim 8, wherein the processor arrangement is configured to:
activate an alert timer when the visual and/or audio reminder is output when the scheduled dosing time is due; and
deactivate the visual and/or audio reminder when the alert timer expires.

11. The packaging assembly of claim 10, wherein an expiry time period for the alert timer is between 5 and 60 seconds.

12. The packaging assembly of claim 1, wherein the wireless communication module is configured to broadcast a wireless connection request in response to detecting that the intensity of light detected by the light sensor exceeds the threshold light intensity.

13. The packaging assembly of claim 12, wherein the wireless communication module, in response to receiving a signal from the at least one external device in response to the broadcast communication request, is configured to determine the identity of the at least one external device and to establish a wireless connection with the at least one external device conditional on the determined identity of the at least one external device.

14. The packaging assembly of claim 1, further comprising:
one or more environmental sensors configured to output a signal representative of environmental conditions external to the case,
wherein the wireless communication module, when a connection to the at least one external device is established, is configured to transmit the signal of the one or more environmental sensors to the at least one external device.

15. The packaging assembly of claim 14, wherein the one or more environmental sensors are configured to detect a temperature or a humidity of an environment external to the case.

16. The packaging assembly of claim 1, further comprising the plurality of injection devices contained within the case, wherein each of the plurality of injection devices contain a medicament.

17. The system of claim 16, wherein the medicament is an anti-IL-4 monoclonal antibody.

18. A method of operating a packaging assembly, the packaging assembly comprising a case configured to at least partially contain a plurality of injection devices for delivering a medicament,
the method comprising:
using a light sensor of the packaging assembly, detecting light incident on the packaging assembly;
using a wireless communication module of the packaging assembly, establishing a wireless connection with at least one external device conditional on an intensity of light detected by the light sensor exceeding a threshold light intensity;
in response to detecting that the intensity of light detected by the light sensor exceeds the threshold amount of light, starting a door open timer, wherein the door open timer is set to expire after a predetermined time; and
using the wireless communication module, transmitting a door open alert to the at least one external device when the door open timer expires.

19. The method of operating a packaging assembly of claim 18, comprising the processor arrangement entering a partial sleep state on expiry of the door open timer.

20. A method of operating a packaging assembly, the packaging assembly configured to be stored in a fridge and comprising a case configured to at least partially contain a plurality of injection devices for delivering a medicament and a processor arrangement, the method comprising:
using a light sensor of the packaging assembly, detecting light incident on the packaging assembly;
the light sensor providing a signal to the processor arrangement according to the detected light intensity;
the processor arrangement determining that a door of the fridge is open in response to determining that the intensity of light detected by the light sensor exceeds a threshold amount of light;
using a wireless communication module of the packaging assembly, establishing a wireless connection with at least one external device; and using the processor arrangement, determining that a scheduled dosing time is due and transmitting an alert to the at least one external device to indicate that the scheduled dosing time is due conditional on the processor arrangement having determined that the fridge door is open.

* * * * *